US011963974B2

(12) United States Patent
Tajima et al.

(10) Patent No.: US 11,963,974 B2
(45) Date of Patent: Apr. 23, 2024

(54) ANTISENSE OLIGONUCLEOTIDE AND COMPOSITION FOR PREVENTION OR TREATMENT OF GLYCOGEN STORAGE DISEASE TYPE Ia

(71) Applicants: NATIONAL CENTER FOR CHILD HEALTH AND DEVELOPMENT, Tokyo (JP); HIROSHIMA UNIVERSITY, Hiroshima (JP); DAIICHI SANKYO COMPANY, LIMITED, Tokyo (JP)

(72) Inventors: Go Tajima, Tokyo (JP); Satoshi Okada, Hiroshima (JP); Miyuki Tsumura, Hiroshima (JP)

(73) Assignees: NATIONAL CENTER FOR CHILD HEALTH AND DEVELOPMENT, Tokyo (JP); HIROSHIMA UNIVERSITY, Hiroshima (JP); DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/491,435

(22) PCT Filed: Mar. 9, 2018

(86) PCT No.: PCT/JP2018/009326
§ 371 (c)(1),
(2) Date: Dec. 17, 2019

(87) PCT Pub. No.: WO2018/164275
PCT Pub. Date: Sep. 13, 2018

(65) Prior Publication Data
US 2020/0246369 A1 Aug. 6, 2020

(30) Foreign Application Priority Data
Mar. 10, 2017 (JP) ................................. 2017-046766

(51) Int. Cl.
*C12N 15/11* (2006.01)
*A61K 31/7088* (2006.01)
*A61K 48/00* (2006.01)
*A61P 3/08* (2006.01)
*C12N 15/113* (2010.01)

(52) U.S. Cl.
CPC .......... *A61K 31/7088* (2013.01); *A61K 48/00* (2013.01); *A61P 3/08* (2018.01); *C12N 15/113* (2013.01); *C12Y 301/03009* (2013.01); *C12N 2310/11* (2013.01); *C12N 2310/3231* (2013.01); *C12N 2310/3233* (2013.01); *C12N 2320/33* (2013.01)

(58) Field of Classification Search
CPC .............. C12N 15/113; C12N 2320/33; C12N 2310/3231; C12N 2310/11; C12N 2310/3233
See application file for complete search history.

(56) References Cited

U.S. PATENT DOCUMENTS

| | | |
|---|---|---|
| 5,627,274 A | 5/1997 | Kole et al. |
| 7,314,923 B2 | 1/2008 | Kaneko |
| 7,335,765 B2 | 2/2008 | Kaneko |
| 7,816,333 B2 | 10/2010 | Kaneko |
| 8,957,201 B2 | 2/2015 | Kaneko |
| 10,745,700 B2 | 8/2020 | Uehara |
| 11,299,736 B1 | 4/2022 | Prakash |
| 2002/0147332 A1 | 10/2002 | Kaneko |
| 2003/0207841 A1 | 11/2003 | Kaneko |
| 2005/0261233 A1 | 11/2005 | Bhanot |
| 2006/0051769 A1* | 3/2006 | Barts ................ C12Q 1/689 435/6.11 |
| 2009/0149404 A1 | 6/2009 | Kaneko |
| 2011/0009471 A1 | 1/2011 | Kaneko |
| 2011/0178283 A1* | 7/2011 | Rigoutsos ........... G16B 20/20 536/24.5 |
| 2012/0190728 A1 | 7/2012 | Bennett et al. |
| 2014/0024698 A1 | 1/2014 | Kole et al. |
| 2015/0126718 A1 | 5/2015 | Prakash |
| 2015/0126719 A1 | 5/2015 | Prakash |

(Continued)

FOREIGN PATENT DOCUMENTS

| CN | 105934515 A | 9/2016 |
|---|---|---|
| EP | 1568769 | 8/2005 |

(Continued)

OTHER PUBLICATIONS

Janice Y. Chou et al.: "Mutations in the glucose-6-phosphatase-[alpha] (G6PC) gene that cause type Ia glycogen storage disease" Human Mutation, vol. 29, No. 7, Jan. 1, 2008, pp. 921-930.
Extended European Search Report for EP Patent Application No. 18764477.8, dated Nov. 16, 2020, 6 pages.
Akanuma, Jun et al., Glycogen storage disease type Ia: molecular diagnosis of 51 Japanese patients and characterization of splicing mutations by analysis of ectopically transcribed mRNA from lymphoblastoid cells. Am J Med Genet. Mar. 13, 2000;91(2):107-12.

(Continued)

*Primary Examiner* — Ekaterina Poliakova-Georgantas
(74) *Attorney, Agent, or Firm* — Casimir Jones, S.C.; Robert A. Goetz

(57) ABSTRACT

The present invention provides a novel antisense oligonucleotide and a composition for preventing or treating glycogen storage disease type Ia. The present invention provides an antisense oligonucleotide which hybridizes with a pre-mRNA sequence derived from a region including at least one of a base at position 42911000, a base at position 42911004, and a base at position 42911005 in a base sequence of human chromosome 17 of GRCh38/hg38 and has activity to inhibit aberrant splicing of pre-mRNA of c.648G>T variant G6PC.

8 Claims, 4 Drawing Sheets
Specification includes a Sequence Listing.

(56) References Cited

U.S. PATENT DOCUMENTS

| | | |
|---|---|---|
| 2015/0126720 A1 | 5/2015 | Prakash |
| 2015/0273016 A1 | 10/2015 | Parenti |
| 2015/0275212 A1 | 10/2015 | Albæk et al. |
| 2015/0291958 A1 | 10/2015 | Albæk |
| 2015/0368642 A1 | 12/2015 | Albæk |
| 2016/0017323 A1 | 1/2016 | Prakash |
| 2016/0076030 A1 | 3/2016 | Prakash |
| 2016/0076032 A1 | 3/2016 | Prakash |
| 2016/0090595 A1 | 3/2016 | Prakash |
| 2016/0090596 A1 | 3/2016 | Prakash |
| 2016/0138025 A1 | 5/2016 | Albæk |
| 2016/0289677 A1 | 10/2016 | Albæk |
| 2016/0376585 A1 | 12/2016 | Manoharan |
| 2016/0376608 A1 | 12/2016 | Chou |
| 2017/0233763 A1 | 8/2017 | Chou |
| 2018/0002693 A1 | 1/2018 | Prakash |
| 2018/0044676 A1 | 2/2018 | Prakash |
| 2018/0216116 A1 | 8/2018 | Albæk et al. |
| 2018/0251764 A1 | 9/2018 | Albæk |
| 2018/0273952 A1 | 9/2018 | Prakash |
| 2018/0273953 A1 | 9/2018 | Prakash |
| 2018/0312846 A1 | 11/2018 | Albæk et al. |
| 2018/0312847 A1 | 11/2018 | Albæk et al. |
| 2019/0017069 A1 | 1/2019 | Chou |
| 2019/0055554 A1 | 2/2019 | Prakash |
| 2019/0055558 A1 | 2/2019 | Uehara |
| 2019/0367914 A1 | 12/2019 | Prakash |
| 2020/0224198 A1 | 7/2020 | Prakash |
| 2020/0248186 A1 | 8/2020 | Albæk et al. |
| 2021/0024923 A1 | 1/2021 | Prakash |
| 2021/0087566 A1 | 3/2021 | Prakash |
| 2021/0130823 A1 | 5/2021 | Prakash |
| 2021/0238601 A1 | 8/2021 | Albæk |
| 2021/0395734 A1 | 12/2021 | Prakash |
| 2022/0025376 A1 | 1/2022 | Albæk |
| 2022/0348914 A1 | 11/2022 | Manoharan |
| 2023/0151365 A1 | 5/2023 | Prakash |

FOREIGN PATENT DOCUMENTS

| | | | | |
|---|---|---|---|---|
| JP | 07-87982 | 4/1995 | | |
| JP | 08-510130 | 10/1996 | | |
| JP | 2000-297097 | 10/2000 | | |
| JP | 2012-530715 | 12/2012 | | |
| JP | 2015-501817 | 1/2015 | | |
| JP | 2016-523515 | 8/2016 | | |
| JP | 2016-529230 | 9/2016 | | |
| JP | 2017-501684 | 1/2017 | | |
| WO | WO 1999/14226 | 3/1999 | | |
| WO | WO 2000/47599 | 8/2000 | | |
| WO | WO-2008109366 A2 | * 9/2008 | ........... | C12N 15/113 |
| WO | WO 2009/073809 | 5/2009 | | |
| WO | WO 2012/168435 | 12/2012 | | |
| WO | WO 2014/076196 | 5/2014 | | |
| WO | WO 2014/109384 | 7/2014 | | |
| WO | WO 2014/179620 | 11/2014 | | |
| WO | WO 2015/006740 | 1/2015 | | |
| WO | WO 2015/105083 | 7/2015 | | |
| WO | WO 2016/055601 | 4/2016 | | |
| WO | 2016/106303 | 6/2016 | | |
| WO | WO 2017/084987 | 5/2017 | | |
| WO | WO-2017077386 A1 | * 5/2017 | ........... | C12N 15/102 |
| WO | WO 2017/106210 | 6/2017 | | |
| WO | WO 2017/131236 | 8/2017 | | |

OTHER PUBLICATIONS

Chou, JY et al., Type I glycogen storage diseases: disorders of the glucose-6-phosphatase/glucose-6-phosphate transporter complexes. J Inherit Metab Dis. May 2015;38(3):511-9.

English Translation of International Preliminary Report on Patentability for PCT/JP2018/009326, dated Sep. 19, 2019, 8 pages.

Havens, MA et al., Targeting RNA splicing for disease therapy. Wiley Interdiscip Rev RNA. May-Jun. 2013;4(3):247-66.

International Search Report for PCT/JP2018/009326, dated Jun. 5, 2018, 2 pages.

Kajihara, Susumu et al., Exon redefinition by a point mutation within exon 5 of the glucose-6-phosphatase gene is the major cause of glycogen storage disease type Ia in Japan, Am. J. Hum. Genet., 1995, vol. 57, pp. 549-555.

Li Jing-yi et al., "A Novel Compound Heterozygous Mutation in Glucose-6-Phosphatase Gene in a Chinese Patient with Glycogen Storage Disease Ia", Medical Journal of Peking Union Medical College Hospital, 2016, 7(4) pp. 264-268, English Abstract.

Office Action for CN Patent Application No. 201880017237.7, dated Nov. 10, 2022, 8 pages.

Rake et al. Eur. J. Pediatr.(2002), vol. 161, Suppl. 1, pp/S20-34.

Shimo, Takenori et al., Nucleic Acids Research, 2014, vol. 42, No. 12, pp. 8174-8187.

Chou, Janice Y. et al Nature Review Endcrinology (2010), vol.6, No.12, p.676-688.

* cited by examiner

EXPECTED LENGTH OF NESTED PCR PRODUCT :
cDNA WITH DELETION = 214 bp   NORMAL LENGTH cDNA = 305 bp

SEQUENCE LISTING

```
<160> NUMBER OF SEQ ID NOS: 29

<210> SEQ ID NO 1
<211> LENGTH: 19572
<212> TYPE: DNA
<213> ORGANISM: Homo sapiens

<400> SEQUENCE: 1
ctgcaattac aggtgccagc cacctcactg ggctattttt tttttttttt ttgaaatagg      60
gtctctttct gtcacccagg ctggagtgta atggtgtgat ctcggctcgc tgcaacttcc     120
acctcctggg ttcgagggat tctcttgcct cagcctcctg agtagctggg attacaggcg     180
cccaccacta cacctggcta attttttgtat ttttagtaga gatggggttt caccatgttg     240
gtcaggctgg tcttgaactc ttgaccttgg gtgatccacc cacctcagcc tcccaaaatg     300
cttggattac aggcgtgagc cactgcacct ggccaatttt tgtatttttt gtagagatgg     360
ggtttcacca tgttggctag gctggtctca aactcctaag ctcaagtgat ccaccaacct     420
```

```
cagcctctca aagtgctggg tttacaggtg tgagccatcg caccaggccg tgactatttt    480
aaataaaaaa cccttgagag gttttttcac ccttgggagc ctggaagaga tttttcccc     540 tatctttcac ctataaagat aggactggcc gggcatggtg gctcatgctt gtaatctcag    600
cactttggga ggccgaggcg ggtggatcac ctgaggtcag gagttcgaga ccagcctggc    660
ccaacatggc aaaaccccat ctctactaaa aatacaaaaa ttaatcgggc ctggtggcac    720
atgcctgtaa tcccagctac ttgggggggct gaggcacagg aatcgtgga tctcaggagg    780 cagaggttgc agtgagccaa gatcatcgca ttgcactcca gcctgggcaa caagagtgat    840
actccgtctc aaaaaaaaaa aaaaaaaagg actgacacaa agaacaatt gttcttctcc     900 ttcctttatc ccattatcca tcacagaaaa gaagaccaaa aatgtaacca taaaaaagtc    960
tcaacagacc cttttcaag acaatgactg tctctgagga ccatttaaaa tccagggaga    1020
actatttaca agttaatttc tgttcctcga tccaatcatt ctccctctgc ccttcgacag   1080
aattcctctt ctcctccttc ccataacctg ttttaacag gatccaagcc acccattctt    1140
tctgcaacct caagatggtg gatgagcttc catacctcac tgggaagttg gatcttcatt   1200
cttaagcctc ccatgtatac atgttaaata catttgtaat cttttctca tattaattaa    1260 tctgccttat gtcagtgact tttcagcgaa cttgtaggta gtcactcaca taaggatcct   1320 ccagttaca tagttttgta aatgtcaggt caccctgtcc cactagacca ccaaggtcct    1380
ggaggacacc tgggatttaa cttttttttt tttttttttt tttgagacag tctcgctctg   1440
tcactgaggc tggagtgcag tgtcaggatc tccactcact gcaacctcca cctcccgggt   1500
ttaagtgatt ctcctgcttc agcctcccga gtagctgaga ctacaggtgc cctcatcat    1560 acccggctaa ttttttatatt tttagtagag atggggtttt gctatattgg ccaggctggt   1620
cttaaactcc tgacctcagg tgatccaccc tcctcagcct cccaaagtgc tgggattaca    1680
ggcgtgagcc accatgccca gcctggcttt taactttta ttcctcagag agccaggcat    1740 ggtgcttgc tcaggaaatg ttggttgaat taaaccggag cacttcttga aaagggaaaa    1800
taacaaagag ttagaaggag atggcgggaa cccctctctg gagatagttc tttaaattag   1860
tggattctgc agggcactgt tgctcatacc tgtaatccca gcattttggg aggccaaggc   1920
aggaggacca cctgatgccg ggagtttgag accagtctgg gcaatgtaga gagaccccca   1980
tctccacaaa aaataaaaag ttagctgggt ttggtggtgt gcgcctgtag gcccagctac   2040
ccagagactg atgcaaaacg atcccttaag cccaggagac tgaggctgca gtgagctgtg   2100
atggtgccac cgcactccag cctgggtaac agagtgagac cccgtctcaa ataaacagat   2160
aaatgagtgg attctcagca aaacttctag ccactcgcct catatatcca caagacctt    2220 gagaatccac ggtgtctcga tgcagtcagc tttctaacaa gctggggcct cacctgtttt   2280
cccacggata aaaacgtgct ggaggaagca gaaaggggct ggcaggtgga aagatgagga   2340
ccagctcatc gtctcatgac tatgaggttg ctctgatcca gagggtcccc ctgcctggtg   2400
gcccaccgcc aggaagactc ccactgtccc tggatgccca gagtgggatg tcaactccat   2460
cacttatcaa ctccttatcc atagggggtat tcttcctgag gcgtctcaga aaacagggcc   2520
ctccccatat gctgaccaca taatagaacc cctcccaact cagagaccct ggctgctagc   2580
tgccctggca tgacccagac agtggccttt gtatatgttt ttagactcac cttgactcac   2640
ctctgaccat agaaactctc atcccagagg tcactgcaat agttactcca caacagaggc   2700
ttatctgggt agagggaggc tccctaccta tgggcccagca gccctgacag tgcagatcac   2760 atataccccca cgccccagca ctgcctgcca cgcatgggct tactttacac ccacccacag   2820
```

```
tcaccaacac attacctgct ctccaaggtt aggcgtggca ggagaagttt gcttggacca    2880
gcagaaacca tgcagtcaag gacaactgga gtcagcatgg gctgggtgcg agcccttggt    2940
ggggtgggga ggagactcca ggtcatacct cctggaggat gttttaatca tttccagcat    3000
ggaatgctgt caacttttgc cacagattca ttagctctga gtttcttttt tctgtcccca    3060
gctacccctt acatgtcaat atggacttaa tgatgggaaa ttcaggcaag ttttaaaca    3120 ttttattccc cctggctctt atcctcaaaa aatgcatgaa tttggaggca gtggctcatg    3180
cctgtaatcc caatgctttg ctaggttgag gcgggaggat cacttgaagc caggaatttg    3240
agaccagcct gggccgcata gtgagacccc gtttctacaa aaataaataa ataataata    3300 aataatagtg atatgaagca tgattaaata gccctatttt ttaaaatgca tgagttcgtt    3360
acctgattca ttccctggtt cctttcacag tcctccgtga cccaagtgtt agggttttgg    3420
tctctctact atttgtaggc tgatatatag tatacacaca cacacacaca cacatataca    3480
cacacacagt gtatcttgag ctttcttttg tatatctaca cacatatgta taagaaagct    3540
caagatatag aagcccttt tcaaaaataa ctgaaagttt caaactcttt aagtctccag    3600 ttaccattt gctggtattc ttatttggaa ccatacattc atcatattgt tgcacagtaa    3660
gactatacat tcattatttt gcttaaacgt atgagttaaa acacttggcc aggcatggtg    3720
gttcacacct gtaatcccag agctttggga agccaagact ggcagatctc ttgagctcag    3780
gaattcaaga ccagcctggg caacatggaa aaacccatc tctacaaaag atagaaaat    3840 tagccaggca tggtggcgtg tgcctgtggt cccagctact caggaggctg aggtgggagg    3900
atcacattag cccaggaggt tgaggctgca gtgagccgtg attatgccac tgcactccag    3960
cctgggagac agagtgagac cctgtttcaa aaaaagaga gagaaatttt aaaaagaaa    4020 acaacaccaa gggctgtaac tttaaggtca ttaaatgaat taatcactgc attcaaaaac    4080
gattactttc tggccctaag agacatgagg ccaataccag gaaggggggtt gatctcccaa    4140 accagaggca gaccctagac tctaatacag ttaaggaaag accagcaaga tgatagtccc    4200
caatacaata gaagttacta tattttattt gttgttttc ttttgttttg ttttgttttg    4260
ttttgttttg ttttagagac tggggtcttg ctcgattgcc caggctgtag tgcagcggtg    4320
ggacaatagc tcactgcaga ctccaactcc tgggctcaag caatcctcct gcctcagcct    4380
cctgaatagc tgggactaca agggtacacc atcacacaca ccaaaacaat tttttaaatt    4440
tttgtgtaga aacgagggtc ttgctttgtt gcccaggctg gtctccaact cctggcttca    4500
agggatcctc ccacctcagc ctcccaaatt gctgggatta caggtgtgag ccaccacaac    4560
cagccagaac tttactaatt ttaaaattaa gaacttaaaa cttgaatagc tagagcacca    4620
agatttttct ttgtccccaa ataagtgcag ttgcaggcat agaaaatctg acatctttgc    4680
aagaatcatc gtggatgtag actctgtcct gtgtctctgg cctggtttcg gggaccagga    4740
gggcagaccc ttgcactgcc aagaagcatg ccaaagttaa tcattggccc tgctgagtac    4800
atggccgatc aggctgtttt tgtgtgcctg ttttctatt ttacgtaaat caccctgaac    4860
atgtttgcat caacctactg gtgatgcacc tttgatcaat acattttaga caaacgtggt    4920
ttttgagtcc aaagatcagg gctggggttga cctgaatact ggatacaggg catataaaac    4980
aggggcaagg cacagactca tagcagagca atcaccacca agcctggaat aactgcaagg    5040
gctctgctga catcttcctg aggtgccaag gaaatgagga tggaggaagg aatgaatgtt    5100
ctccatgact ttgggatcca gtcaacacat tacctccagg tgaattacca agactcccag    5160
```

```
gactggttca tcttggtgtc cgtgatcgca gacctcagga atgccttcta cgtcctcttc   5220
cccatctggt tccatcttca ggaagctgtg ggcattaaac tcctttgggt agctgtgatt   5280
ggagactggc tcaacctcgt ctttaagtgg taagaaccat atagagagga gatcagcaag   5340
aaaagaggct ggcattcgct ctcgcaatgt ctgtccatca gaagttgctt tccccaggct   5400
attcaggaag ccacgggcta ctcatgcttc caacccctct ctctgacttt ggatcatcta   5460
cataaagggg gaagacagaa aaaatcctac cagtgagttg aaaatacagg aaagcctatt   5520
tcatatgggt taaagggtag gacagttgaa tttcgtgaaa agtctgagtt atataggctt   5580
tgagcaaaga gttttattag tatgaagcag aagaggtaac ataaagaaag atgtatgggg   5640
ccaggcatgg tggctcacac ctgtaatccc agcactttgg gaggccgagg tgggcgaatc   5700
actcctgggt gaactcagga gttcaagacc agcctgggca acatggcgaa actccatctc   5760
tacaaaaaca ttacgaaaat tagctgggcg tgttggtgct gtagtcccag ctactcagga   5820
ggctgaggtg agaggcggag gaggttgcag tgagtcaaga tcatgccact gcactccagc   5880
ctgggcaaca gagtaagacc ctgtctcaaa aaaaaaaaaa agatagatga tgtatgctgt   5940
atgaaaaaag gaaacacaca gatgattcaa cagcctgttt tgtggggtaa tgaaaagtca   6000
ccctgggaac tgggctccag ccctcgttct gccacccacc aactacatgt ccttggcaag   6060
tcatatcaat tatctgagtt tctgttttat aatctacaaa taggttatct ctggcagctt   6120
aataataatc agggttaaca tttattaaac agtgtgtgcc agtccatgtg ctatgtgctt   6180
ttctgtgagg tagttactgc tatttacaga aacagtagat gcagagacca aggtgctgag   6240
ttaaatgatt aggccaacaa ggttagtaca tgccgagcca ggatggaagc ccaggtaggc   6300
aggctggctt ccgcggcaat gctcttatga actatgttac gtccagtgct gataaactga   6360
ctctctgggg agcaggggaa agccctgagt ttagcatttg ccaatttcta tcacgtaaac   6420
attcccattc tggccacttt cttttctttct ttcttttgtt tgtttgtttg agatggagtc   6480
tcgcactgtt gcctggctgg agtgcaatgg tgcaatctca gctcactgca acctctgcct   6540
ctccggttca agtgattctc ctgcctcagc ctcccaagta gctgggatta caggtgcccg   6600
ccaccatgcc cagctaattt ttttttgtatt tttagtagag acatggtttc actatgttga   6660
ctaggctggt ctcgaactcc tgacctcatg atctgcctgc cttggcctcc ctaagtgcta   6720
ggattacagg cgtgagccac tacacccagc cgcatgattc taaaaaataa aaagatgaag   6780
tgttattcca aacatctgat ctccattgaa gaaccatgca atctctctgg gttgatagag   6840
gccagagtta gtggctctcc ctgatttcgg tgagaaatca ctattccacc atcacgggat   6900
aaaaggcatc ctgactggcg gttgacacct atttccacag tgaaagatat atctagtact   6960
tttaaagggg aagtggtttg tctgagatac tctgtttcaa agtagagagg atacagaaca   7020
agcatctgaa gctatataca tccttacaga gagcaattct gatggaaatg caggccatgt   7080
ttccctgggg gggctcgtc ctaggggctg gagtgcattc tctgatgtca gaggaaatgc   7140
aagattccct gaggcctgag ggaacccatg gtatatgcaa gtccaagttt caaactgtag   7200
ttccatatgc attcttccag gacaaatact tcttgaggtt aaaaaaaaaa agtcacatag   7260
ctgccatttt atggatttca ggattttttt tttttttttt ttgagatgga gtcttgctct   7320
gtcacccagc ctgtagtgca gtggcataat ctcggctcac ggcaacctcc gcctcccagg   7380
ttcaagcgat tctcttgcct tagcctcccg agtagctggg attacagtca cgcaccacca   7440
catctggcta attcttttata tttttttggta gaaacggtgt ttcaccatgt tggccaggct   7500
ggtctcaaac tcctgaccta catgtgatctg cctgccttgg cctcccaaag tgctgagatt   7560
```

-continued

```
acaggtgtga gccaccgcgc ctgcctggag ttcagaatct tgggcttcat tatttgtgtt    7620
taaatagatc atacagtcag gcacggtggc tcatgcctgt aatcccagca ctttgggagg    7680
ctgaggtggg aggattgcct gagttcagga gatggagacc agcctgggca acatggtgaa    7740
accccgtctc tactaaaaat acaaaaacta gctggatgtg gtggcacaca cctgtagtcc    7800
cagctattca ggaggctgag gtgggaggat cccaggaggt agaggtcaca atgagccgag    7860
attgcgccac tgcactccag gctgggttac tgagccagat cctgtctcaa aaaaaaaaa    7920 gataatacat tcaaacagtt caaaatgcaa agttacata cataaggaag tgtcatgaaa    7980
tatctccctc tcacacttct ccccagccac ccagttctcc cttctagagg caacatgtga    8040
aatccttctc aggctacact cttcttgaag gtgtaggctt tgggcaaaag cattcattca    8100
gtaaccccag aaacttgttc tgtttttcca taggattctc tttggacagc gtccatactg    8160
gtgggttttg gatactgact actacagcaa cacttccgtg cccctgataa agcagttccc    8220
tgtaacctgt gagactggac caggtaagcg tcccagcccc tgcagacaga agctgagtgg    8280
acctcgttta cctgttatgg atgaaactga ccttgagggg acatgaggag agccattcct    8340
ttgtactttt gtcatgctct tcaattggca caaattaatt cacttctgca atactttcct    8400
gaatagcaca gtagtattgg aaatctgcct attacagaac ctggatggag tccagagagg    8460
cacgggcatc catgggcaaa gggctcgtga gagtcaccgc cctgcagcgc tgtgtcctga    8520
gaaaggaggg ggcagaagcc tgagcttctg ggggtccttc ccaatggcct ggcccactgg    8580
atgtgccctc ctgagctgac cgtccaatcc cttgccctct ctgtgcctac gtttattag    8640 ttacagccag atggttactg tcaaatcaaa tgatagattt cattttcagt atgtaatagg    8700
aagcccctcc ctcacccctaa agtctcagct gccctctaag actagtactc tctaaggtac    8760
tagtatccct tcctcagaga ccctttccct gaccccaaaa ctagggaagg tcccttagtt    8820
atttgctctc acagaccacg catttacctc agagcatatt cactcattca gctgttactt    8880
accaagcacc tactgggagc tatacactgt tctatgtgct agggatacct ctgtcagtga    8940
acaacacaga cacaaagatc cctgcccttg tggagctgaa atctgaatag aggaggtgaa    9000
atatacaaaa attataataa ataagtaaac taggccagtt gtggttgctc atgcctgtaa    9060
tcccagcact ttgggaagcc aaggtaggta gatcacctga ggtcaggagt tcaaaccag    9120 cctggccaac attgcaaaat cctgtcttta ctaaaaatgg aaaaattggt caggcgtgat    9180
ggcacacgcc tgtagtctca gctacctggg aggctgaggc aggagaatcg cttgaacctg    9240
ggaggcagag gttgcagtga accgagatcg gaccactgca ctccagcctg aatgacagaa    9300
cgagactctg tctcaaaaaa aaagtaaact attaatatgt aggataggcc aggcacggtg    9360
gctcaccctg taatcccagc actttgggag gctgaggcgg gtggatcacc tgaggtgagg    9420
agttcaagac cagcctggcc aacatggcaa aaccctgtct ctactaaaaa tacaaaaatt    9480
agctgggtgt cctggtgcat gcctgtaatc tgagctactc aggaggctaa gcaggagaa    9540 tcgcttgaac ctgggaggtg gtgagccaag attgcgccat tgcactccag cctgggcgac    9600
aaaatgagac accatctgaa aaaaaaaaa aaatatatat atatatacac acacacacac    9660
acacacacac acacacacat ataatactag aaaatgattg tttataggca aaaaaaaaa    9720 aaagaagaa gaagaagaaa aggaaaggag aaggaaagaa ggaccaaaca tcttttgtag    9780
aaatatgttt gctttcatca taacagcttg ttatcaagga tgaatttctc cctgaaatta    9840
atggaggcac agactggaaa gtttaaagtg gctttaagag gttatttat ttagtcctct    9900
```

```
gtcttaatag aagcaaatta ttatctctgc tccttaggta gagtagctaa ggctcagaaa    9960
gtaggccggg cgcggtggct cacgcctgta atcctagcac tttgggaggc caacgcaggt   10020
ggatcacctg aggtcaggag tttgagacca gcctggccaa catggtgaaa cctcgtcact   10080
aataaaaaaa tacaaaaact tagccaggca tggtggcggg cgcctgtaat cccagctacc   10140
caggaggctg cggcaggaga atcacttcaa cccgggaggc agaggttgca gtgagctgaa   10200
atcacaccac tgcactccag ccttggtgac agagaaagat tctgtcagga aaaaaaaaa   10260 aaagtttaaa tgaattaccc aaggtatata attgttagtg ttagaaggaa gagaagga   10320 gggaggaagg aagggagaaa gaagggaag gaggaaggga gggagggaag aaagccttta   10380
tttatctatg gggttccctg gaaagcaggc tgaaatggag attcacgtgc aggagtttag   10440
atactctggg gaactatact tgtagaaggg aaggaacagg aacagggcag aaggagaggt   10500
ccggttgtga ttctgcctca tccaaccca cagcgagctc tgaagctggg gatggctcct   10560
cagagttggt ccaagttggg acaagggaat cagaccctgg ggagagcgta accttgatca   10620
aggcgactct ctttagccca gggcaatgcc aggagaaggc tgagagcaga aagccatcta   10680
ccatcacact ctcaacagct acgaaataag tcctgcagtt caggagggag gtctgggcgg   10740
cacatctcag gaccctctat ctctcagggt agaggaatta agaatgggat gggaaccaga   10800
cgggccatgg tggctcacac ctataatccc aacactttgg gaggccaagg gtaggaggat   10860
tgcttgagcc caagagttca aaccagcct gggcaaaaac aatcaaacaa acaaacaaaa   10920
cacatttaaa aaatttgctg tgtgtggtgg tgtgcacctg tggtcccagc tactcagggg   10980
gctgaggtgg gaggattgct tgagtccagg aggtcgaggc tgcagtgagc tatgatcatg   11040
gcactgcatt gcagcctagg agacaaagca agacactgtc tctaaaaaaa caaaaaacaa   11100
acaaataaaa aaacggaacc ggttgcaagc agggttaaat agcgtggtca gagtaggact   11160
cactgagaat atgagatctg agtcaagtct tcaaggatgt gaggaagtaa gtttctggca   11220
gaagagctgt gaagggctgt ctggccagag aagattgcaa tgcaaaagcc ctgaggtggg   11280
aacgtgtttg gtgtgtttaa aggaaagcaa tgaggccagt gtagccagaa cagagtgtgc   11340
aaggagagaa ggaacagaag atgtggaggg cagatcagtt tgtaattgta cgcccagtat   11400
gctgattctt tgtgtaatct ccagactgta ttaaactgca agagcagggc ccctctctgg   11460
ctttgctcat cattgtattc ccagagcctt gcacaatgct tggtgcatag agatggaaa   11520 tttgttaaat aaatgaatta tggataacga atggatggta agatgggtgg atggatgggg   11580
ggtgaacgga tggatggggg gtgaatggat ggatgaatgg gtagatgggt ggataggggg   11640
atggctgggt ggctgggtag atgatgcact gtctcccaga tgaggacctt tcacccttta   11700
ctccattctc tttcctgccc tttagggagc ccctctggcc atgccatggg cacagcaggt   11760
gtatactacg tgatggtcac atctactctt tccatctttc agggaaagat aaagccgacc   11820
tacagatttc ggtaagaact caccactggg gtgtaggtgg tggagggcag gaggcagctc   11880
tctctgtagc tgacacacca cgtattcttc ctcacatccc cctagcccgc tcccacacct   11940
gggcagccgc tgattaagag ttgtggcact ttggataggg ataaacctca gagtcaggga   12000
atgtttgggc tgaaagggat ccagtagtgc aatccgttgt tttacagata aggaaacaaa   12060
gcccaacacc atgaagggac ttataaaaat aaggtagtga agtagcagca gggcttaaat   12120
aaaaacccat gtctgtacca accacagagt cacccatcca ggttaaaata accagagaaa   12180
cagaagatat tcctactaca gagaattccg ggtgtgcagc cacagtgcaa atcctttta   12240 tttttatttt tgagatgcag tctcgctctg tcatccaggc tgaagtgcag tggcacgatc   12300
```

```
atgtctcgct gcaacctctg cctcccaggc tcaagcgatc ctcccacctc agccatctga   12360
gtagctggga ccacaggcca cacaccacac ccagctaatt tctcgtatct ttttgtagag   12420
acagagttct gctatgttgc ccaggctcag gctggtcttg atctcaagca attggcttgc   12480
ctcagcctcc taaaatattg ggattacagg catgagccac cgcgccagcc atgcaaatcc   12540
ttaattatca aacagataaa atagggaagt taaaattcat atacacaagg gttaaccact   12600
tgccacaggc atttttttt ttttttgag acggaatctc gctctgttgc ccaggctgga   12660
gtgcagtggc gccatctcgc tcactgcaa cctccgcttc ctgggttcaa gctattcttc   12720
tgcctcagcc taccgagtag ctgggactac aggcacgtgc caccacacct ggctaatttt   12780
tttattttta gtagagatgg ggtttcacca tattggccag gctggtcttg aactcctgac   12840
ctagtgatcc atccgcctca gcctcccaaa gtgctgggat tgcaggcatg agccaccgcg   12900
cctggccttt tttttttttt tttgagacgg agttttgctc ttgttgccca ggctagagtg   12960
cagtggcgca gtctcggctc actgtaacct ccacctcctg agttcaagca attctcctgc   13020
ctcagcctct caaatagctg ggattacagg cgtgagccac cccacctggc taattttgta   13080
attttttttt tagtagagat ggggtttcac ctgttgatca ggctggtctc aaactcctga   13140
cctcaagtga tccaccccacc tcggcctccc aaagtgctgg gattacaagc ataagccacc   13200
gtgcctggtc aattttgatc tttttaaag acagggggt cttgctatgt tgcccagact   13260
agtcttgaac tcctggcctc aagtgatcct ctcacctcgg cctcccaaag tattgggatt   13320
acaggtctga ccgctgcac ccagccccca acaggcatct ttggacttt gagtactggc   13380 tttaatttac aaaaattcca ctgagagcac ctaagtttgc caggctccaa catttctgca   13440
ggggctgttt tctttgctga aggatctgca cctgtgttct gttatggttg cctcttctgt   13500
tgcaggtgct tgaatgtcat tttgtggttg ggattctggg ctgtgcagct gaatgtctgt   13560
ctgtcacgaa tctaccttgc tgctcatttt cctcatcaag ttgttgctgg agtcctgtca   13620
ggtatgggct gatctgactc ccttccttct cccccaaacc ccattccgtt tctctcccta   13680
atcaggacaa aatcccagca ttccagccac atcctgtgtg taatcagtac tgttagcatt   13740
tctgtgggtt gaaagtcaag aatgagcaac ttgaaatgat taatttctat aagagtgccc   13800
agatctatag aatgaattgt gtagaagtta ccatacatca aattaacgca ccaaattgaa   13860
ttagcttgaa atctcagagc tttttacaat ctttatttct tactggtctt caacaggccc   13920
taatttactt ttcagggaat ctgccaaatt taacaaatta acacgatgtc ctaggaaagc   13980
tgttcattta aatacattca tttgcaaacc taatagataa ctgcagttga tctctttat   14040 aggttcagag ttttgaatat gtttttttt gtttttttt tttgagatgg agtctcgctc   14100
tgtgacccag gctagagtgc agtggtgcga tctcggctca ctgcaagctc cacctcctgg   14160
gttcacgcca ttctcctgcc tcagcctctc cgagtagctg ggactacagg cgcccgccac   14220
catgcccggc taatttttg tatttttagc agagacgggg tttcaccgtg tcttgatct   14280 cctgacctcg tgatccgccc gcctcggcct cccaaagcgc tgggattaca gggtgagcc   14340 accgcaccct gcctgaatat gtgttttctt agatccaatt aacaagggta agacaagatt   14400
taagttaagc ataagaaaga ttttgtggga ggcactggaa tataagacct taacaaaact   14460
gtggaatttc tccctggag atttgtaaga acggaacata gcagcattca aagaagaatg   14520
ttgagaacaa gggagataat ggtttcatgg taatcacaaa agtaacacag catttagtac   14580
tgggttccat gtttgaggaa gaacctggaa gccatatcac atgaaaaacc tgggaatgtt   14640
```

```
taggttagag agaataactg tgttcaaatg tgtgacagag ggactagatt catcacttac    14700
taactcctgc agaaagaact gagaaaaata gacagtatta gaggggggacc agtttcacac    14760 agacaaggaa gaactattca gcaatcaatt ccgttcaaag ataaaatgga ctgttatagt    14820
gggggtgagc tccctacctc tgagggtatt tcaagtagag ataggaggac ctcctggtag    14880
gaaatttgca tacggtggga gattgtacgt gatatggcac ctccatctga aagagtctat    14940
attgagggca ggctggagtc acacatggga ataagccagg cgaccctccc atctgccatc    15000
tgtgatttaa ttccacagtc gcagaacgga tggcatgtca cccactcctc caaacccacc    15060
tctagcaaag gtcccaaatc cttcctatct ctcacagtca tgctttcttc cactcaggca    15120 tgctgttac agaaactttc agccacatcc acagcatcta taatgccagc tcaagaaat    15180 attttctcat taccttcttc ctgttcagct tcgccatcgg attttatctg ctgctcaagg    15240
gactgggtgt agacctcctg tggactctgg agaaagccca gaggtggtgc gagcagccag    15300
aatgggtcca cattgacacc acacccttg ccagcctcct caagaacctg gcacgctct    15360 ttggcctggg gctggctctc aactccagca tgtacaggga gagctgcaag gggaaactca    15420
gcaagtggct cccattccgc ctcagctcta ttgtagcctc cctcgtcctc ctgcacgtct    15480
ttgactcctt gaaaccccca tcccaagtcg agctggtctt ctacgtcttg tccttctgca    15540
agagtgcggt agtgccctg gcatccgtca gtgtcatccc ctactgcctc gcccaggtcc    15600
tgggccagcc gcacaagaag tcgttgtaag agatgtggag tcttcggtgt ttaaagtcaa    15660
caaccatgcc agggattgag gaggactact atttgaagca atgggcactg gtatttggag    15720
caagtgacat gccatccatt ctgccgtcgt ggaattaaat cacggatggc agattggagg    15780
gtcgcctggc ttattcccat gtgtgactcc agcctgccct cagcacagac tctttcagat    15840
ggaggtgcca tatcacgtac accatatgca agtttcccgc caggaggtcc tcctctctct    15900
acttgaatac tctcacaagt agggagctca ctcccactgg aacagcccat tttatctttg    15960
aatggtcttc tgccagccca ttttgaggcc agaggtgctg tcagctcagg tggtcctctt    16020
ttacaatcct aatcatattg ggtaatgttt ttgaaaagct aatgaagcta ttgagaaaga    16080
cctgttgcta gaagttgggt tgttctggat tttcccctga agacttactt attcttccgt    16140
cacatataca aaagcaagac ttccaggtag ggccagctca caagcccagg ctggagatcc    16200
taactgagaa ttttctacct gtgttcattc ttaccgagaa aaggagaaag gagctctgaa    16260
tctgatagga aagaaggct gcctaaggag gagtttttag tatgtggcgt atcatgcaag    16320
tgctatgcca agccatgtct aaatggcttt aattatatag taatgcactc tcagtaatgg    16380
gggaccagct taagtataat taatagatgg ttagtggggt aattctgctt ctagtatttt    16440
ttttactgtg catacatgtt catcgtattt ccttggattt ctgaatggct gcagtgaccc    16500
agatattgca ctaggtcaaa acattcaggt atagctgaca tctcctctat cacattacat    16560
catcctcctt ataagcccag ctctgctttt tccagattct tccactggct ccacatccac    16620
cccactggat cttcagaagg ctagagggcg actctggtgg tgcttttgta tgtttcaatt    16680
aggctctgaa atcttgggca aaatgacaag gggagggcca ggattcctct ctcaggtcac    16740
tccagtgtta ctttaattc ctagagggta aatatgactc ctttctctat cccaagccaa    16800
ccaagagcac attcttaaag gaaaagtcaa catcttctct ctttttttttt tttttttgaga    16860 cagggtctca ctatgttgcc caggctgctc ttgaattcct gggctcaagc agtcctccca    16920
ccctaccaca gcgtccgcg tagctgggac tacaggtgca agccactatg tccagctagc    16980
caactcctcc ttgcctgctt ttctttttttt ttcttttttt gagacggcgc acctatcacc    17040
```

```
caggctggag tggagtggca cgatcttggc tcactgcaac ctcttcctcc tggttcaagc    17100
gattctcatg tctcagcctc ctcagtagct aggactaccg gcgtgcacca ccatgccagg    17160
ctaattttta tattttagta attttagaag agatgggatt tcatcatgtt ggccaggctg    17220
gtctcgaact cctgacctca agtgatccac ctgccttggc ctcccaaggt gctaggatta    17280
caggcatgag ccaccgcacc gggccctcct tgcctgtttt tcaatctcat ctgatatgca    17340
gagtatttct gccccaccca cctacccccc aaaaaagct gaagcctatt tatttgaaag     17400
tccttgtttt tgctactaat tatatagtat accatacatt atcattcaaa acaaccatcc    17460
tgctcataac atctttgaaa agaaaaatat atatgtcag tatttatta aagcaacatt      17520 ttatttaaga ataaagtctt gttaattact atattttaga tgcaatgtga tctgaagttt    17580
ctaattctgg cccaactaaa tttctagctc tgtttcccta acaaataat ttggtttctc     17640 tgtgcctgca ttttcccttt ggagaagaaa agtgctctct cttgagttga ccgagagtcc    17700
cattagggat agggagactt aaatgcatcc acagggcac aggcagagtt gagcacataa     17760
acggaggccc aaaatcagca tagaaccaga aagattcaga gttggccaag aatgaacatt    17820
ggctaccaga ccacaagtca gcatgagttg ctctatggca tcaaattgca acttgagagt    17880
agatgggcag ggtcactatc aaattaagca atcagggcac acaagttgca gtaacacaac    17940
aagactaggc cagctctgga atccagtaac tcagtgtcag caaggttttg ggttatagtt    18000
caagaaagtc taaacagagc cagtcacagc accaaggaat gctcaaggga gctattgcag    18060
gtttctctgc taagagattt atttcatcct gggtgcaggg ttcgacctcc aaaggcctca    18120
aatcatcacc gtatcaatgg atttcctgag ggtaagctcc gctatttcac acctgaactc    18180
cggagtctgt atattcaggg aagattgcat tctcctactg gatttgggct ctcagagggc    18240
gttgtgggaa ccaggcccct cacagaatca aatggtccca accagggaga aagaaaatag    18300
tctttttttt ttttttaata gagatgggg tctcactatg ctgcccaggc tggtcttgaa      18360
ctcctgggtt caagtgatcc tcctgcctca gcctcccaaa gtgctgggat tacagtgtga    18420
gccactgcgc ttggccagaa atggttttga tctgtctgaa ctgaacccta ctgcttaggc    18480
atagccccat ccttgataat ctatttgctc ccaaggacca agtccaagat ccttacaaga    18540
aaggtctgcc agaaagtaaa tactgccccc actccctgaa gtttatgagg ttgataagaa    18600
aacataacag ataaagttta ttgagtgcta actttatgcc agattctgtt ctatgtactt    18660
tatttataca attaactcgc ttagttctcc caacatctct gtgagttggc tactgtcatt    18720
tatccttata ttacaaatag gtccagaggg gttagtcatc ttgtccagaa tggtggaacc    18780
aggttaagga tcaggcagtc tgggctgggc atggtggctc acatctgtaa tcccagcact    18840
ttgggaggct gaggtggcag attgcctgag ctcaggagtt cgagaccagc ctgggcaaca    18900
tggtgagacc cccgtctata ccaaaaatac aaaacattag ccaagcgtgg tggtgcatgc    18960
ctgtggtcct aactactcag gtggctgagg tgggagaatc ccttgagctc agaggttgca    19020
gtgagccaag attatgccac tgcactccag cctgggtgac agagtgagac cctgtctcag    19080
aaaaaaaaaa aaaaaagaag caagcagtct gggctgggtg ctgtggctcg cgcctgtaat    19140
cccagataca aaataatcat tttgtaatat atcctgctta ttagacagaa cattttgatc    19200
actcatctgt tccctaagtt atagatttac gtccacttta gaaatggctt gtgaggcaag    19260
tttaagtgac cgatgacagt tttaaagcaa ggtccatgtc atgttatggc ataatttggt    19320
agaatgttct agtagtgtat cagttttcag gtggtaggct tgaggatgat acacacacac    19380
```

-continued

```
acacacgcaa tgcaattcta ttattgccca aagaaaatag acccattaag gaagtccaac    19440
ttctgctgcg tggaccagtg ctgccacatc acacatagac caaaggctta ggttttttgtg   19500 gttttggtta tttattttat ctttttattt tattttatct tattttattt tattttattt   19560
tattatttga ga                                                        19572
```

<210> SEQ ID NO 2
<211> LENGTH: 2382
<212> TYPE: DNA
<213> ORGANISM: Homo sapiens

<400> SEQUENCE: 2

```
tgcaagggct ctgctgacat cttcctgagg tgccaaggaa atgaggatgg aggaaggaat      60
gaatgttctc catgactttg ggatccagtc aacacattac ctccaggtga attaccaaga    120
ctcccaggac tggttcatct tggtgtccgt gatcgcagac ctcaggaatg ccttctacgt    180
cctcttcccc atctggttcc atcttccagga agctgtgggc attaaactcc tttgggtagc   240
tgtgattgga gactggctca acctcgtctt taagtggatt ctctttggac agcgtccata    300
ctggtgggtt ttggatactg actactacag caacacttcc gtgcccctga taaagcagtt    360
ccctgtaacc tgtgagactg gaccaggag ccctctggc catgccatgg gcacagcagg      420
tgtatactac gtgatggtca catctactct ttccatcttt cagggaaaga taaagccgac    480
ctacagattt cggtgcttga atgtcatttt gtggttggga ttctgggctg tgcagctgaa    540
tgtctgtctg tcacgaatct accttgctgc tcattttcct catcaagttg ttgctggagt    600
cctgtcaggc attgctgttg cagaaacttt cagccacatc cacagcatct ataatgccag    660
cctcaagaaa tattttctca ttaccttctt cctgttcagc ttcgccatcg gattttatct    720
gctgctcaag ggactgggtg tagacctcct gtggactctg gagaaagccc agaggtggtg    780
cgagcagcca gaatgggtcc acattgacac cacacccttt gccagcctcc tcaagaacct    840
gggcacgctc tttggcctgg gctggctct caactccagc atgtacaggg agagctgcaa    900
ggggaaactc agcaagtggc tcccattccg cctcagctct attgtagcct ccctcgtcct    960
cctgcacgtc tttgactcct tgaaaccccc atcccaagtc gagctggtct tctacgtctt   1020
gtccttctgc aagagtgcgg tagtgcccct ggcatccgtc agtgtcatcc cctactgcct   1080
cgcccaggtc ctgggccagc cgcacaagaa gtcgttgtaa gagatgtgga gtcttcggtg   1140
ttcaaagtca acaaccatgc cagggattga ggaggactac tatttgaagc aatgggcact   1200
ggtatttgga gcaagtgaca tgccatccat tctgccgtcg tggaattaaa tcacggatgg   1260
cagattggag ggtcgcctgg cttattccca tgtgtgactc cagcctgccc tcagcacaga   1320
ctctttcaga tggaggtgcc atatcacgta caccatatgc aagtttcccg ccaggaggtc   1380
ctcctctctc tacttgaata ctctcacaag tagggagctc actcccactg aacagccca    1440 ttttatcttt gaatggtctt ctgccagccc attttgaggc cagaggtgct gtcagctcag   1500
gtggtcctct tttacaatcc taatcatatt gggtaatgtt tttgaaaagc taatgaagct   1560
attgagaaag acctgttgct agaagttggg ttgttctgga ttttcccctg aagacttact   1620
tattcttccg tcacatatac aaaagcaaga cttccaggta gggccagctc acaagcccag   1680
gctggagatc ctaactgaga attttctacc tgtgttcatt cttaccgaga aaggagaaa    1740 ggagctctga atctgatagg aaaagaaggc tgcctaagga ggagttttta gtatgtggcg   1800
tatcatgcaa gtgctatgcc aagccatgtc taaatggctt taattatata gtaatgcact   1860
ctcagtaatg ggggaccagc ttaagtataa ttaatagatg gttagtgggg taattctgct   1920
```

-continued

| | |
|---|---|
| tctagtattt tttttactgt gcatacatgt tcatcgtatt tccttggatt tctgaatggc | 1980 |
| tgcagtgacc cagatattgc actaggtcaa aacattcagg tatagctgac atctcctcta | 2040 |
| tcacattaca tcatcctcct tataagccca gctctgcttt ttccagattc ttccactggc | 2100 |
| tccacatcca ccccactgga tcttcagaag gctagagggc gactctggtg gtgcttttgt | 2160 |
| atgtttcaat taggctctga aatcttgggc aaaatgacaa ggggagggcc aggattcctc | 2220 |
| tctcaggtca ctccagtgtt acttttaatt cctagagggt aaatatgact cctttctcta | 2280 |
| tcccaagcca accaagagca cattcttaaa ggaaaagtca acatcttctc tcttttttt | 2340 |
| ttttttttt gagacagggt ctcactatgt tgcccaggct gc | 2382 |

<210> SEQ ID NO 3
<211> LENGTH: 2381
<212> TYPE: DNA
<213> ORGANISM: Homo sapiens

<400> SEQUENCE: 3

| | |
|---|---|
| tgcaagggct ctgctgacat cttcctgagg tgccaaggaa atgaggatgg aggaaggaat | 60 |
| gaatgttctc catgactttg ggatccagtc aacacattac ctccaggtga attaccaaga | 120 |
| ctcccaggac tggttcatct tggtgtccgt gatcgcagac ctcaggaatg ccttctacgt | 180 |
| cctcttcccc atctggttcc atcttcagga agctgtgggc attaaactcc tttgggtagc | 240 |
| tgtgattgga gactggctca acctcgtctt taagtggatt ctctttggac agcgtccata | 300 |
| ctggtgggtt ttggatactg actactacag caacacttcc gtgcccctga taaagcagtt | 360 |
| ccctgtaacc tgtgagactg gaccagggag cccctctggc catgccatgg gcacagcagg | 420 |
| tgtatactac gtgatggtca catctactct ttccatcttt cagggaaaga taaagccgac | 480 |
| ctacagattt cggtgcttga atgtcatttt gtggttggga ttctgggctg tgcagctgaa | 540 |
| tgtctgtctg tcacgaatct accttgctgc tcatttcct catcaagttg ttgctggagt | 600 |
| cctgtcaggc attgctgttg cagaaacttt cagccacatc cacagcatct ataatgccag | 660 |
| cctcaagaaa tattttctca ttaccttctt cctgttcagc ttcgccatcg gattttatct | 720 |
| gctgctcaag ggactgggtg tagacctcct gtggactctg gagaaagccc agaggtggtg | 780 |
| cgagcagcca gaatgggtcc acattgacac cacccctt gccagcctcc tcaagaacct | 840 |
| gggcacgctc tttggcctgg ggctggctct caactccagc atgtacaggg agagctgcaa | 900 |
| ggggaaactc agcaagtggc tcccattccg cctcagctct attgtagcct ccctcgtcct | 960 |
| cctgcacgtc tttgactcct tgaaaccccc atcccaagtc gagctggtct tctacgtctt | 1020 |
| gtccttctgc aagagtgcgg tagtgcccct ggcatccgtc agtgtcatcc cctactgcct | 1080 |
| cgcccaggtc ctgggccagc cgcacaagaa gtcgttgtaa gagatgtgga gtcttcggtg | 1140 |
| ttcaaagtca acaaccatgc cagggattga ggaggactac tatttgaagc aatgggcact | 1200 |
| ggtatttgga gcaagtgaca tgccatccat tctgccgtcg tggaattaaa tcacggatgg | 1260 |
| cagattggag ggtcgcctgg cttattccca tgtgtgactc cagcctgccc tcagcacaga | 1320 |
| ctctttcaga tggaggtgcc atatcacgta caccatatgc aagtttcccg ccaggaggtc | 1380 |
| ctcctctctc tacttgaata ctctcacaag tagggagctc actcccactg gaacagccca | 1440 |
| ttttatcttt gaatggtctt ctgccagccc attttgaggc cagaggtgct gtcagctcag | 1500 |
| gtggtccctct tttacaatcc taatcatatt gggtaatgtt tttgaaaagc taatgaagct | 1560 |
| attgagaaag acctgttgct agaagttggg ttgttctgga ttttcccctg aagacttact | 1620 |

| | |
|---|---:|
| tattcttccg tcacatatac aaaagcaaga cttccaggta gggccagctc acaagcccag | 1680 |
| gctggagatc ctaactgaga attttctacc tgtgttcatt cttaccgaga aaaggagaaa | 1740 |
| ggagctctga atctgatagg aaaagaaggc tgcctaagga ggagttttta gtatgtggcg | 1800 |
| tatcatgcaa gtgctatgcc aagccatgtc taaatggctt taattatata gtaatgcact | 1860 |
| ctcagtaatg ggggaccagc ttaagtataa ttaatagatg gttagtgggg taattctgct | 1920 |
| tctagtattt tttttactgt gcatacatgt tcatcgtatt tccttggatt tctgaatggc | 1980 |
| tgcagtgacc cagatattgc actaggtcaa acattcagg tatagctgac atctcctcta | 2040 |
| tcacattaca tcatcctcct tataagccca gctctgcttt ttccagattc ttccactggc | 2100 |
| tccacatcca ccccactgga tcttcagaag gctagagggc gactctggtg gtgcttttgt | 2160 |
| atgtttcaat taggctctga atcttgggc aaaatgacaa ggggagggcc aggattcctc | 2220 |
| tctcaggtca ctccagtgtt acttttaatt cctagagggt aaatatgact cctttctcta | 2280 |
| tcccaagcca accaagagca cattcttaaa ggaaaagtca acatcttctc tcttttttt | 2340 |
| tttttttttg acagggtc tcactatgtt gcccaggctg c | 2381 |

<210> SEQ ID NO 4
<211> LENGTH: 1074
<212> TYPE: DNA
<213> ORGANISM: Homo sapiens

<400> SEQUENCE: 4

| | |
|---|---:|
| atggaggaag gaatgaatgt tctccatgac tttgggatcc agtcaacaca ttacctccag | 60 |
| gtgaattacc aagactccca ggactggttc atcttggtgt ccgtgatcgc agacctcagg | 120 |
| aatgccttct acgtcctctt ccccatctgg ttccatcttc aggaagctgt gggcattaaa | 180 |
| ctcctttggg tagctgtgat tggagactgg ctcaacctcg tctttaagtg gattctcttt | 240 |
| ggacagcgtc catactggtg ggttttggat actgactact acagcaacac ttccgtgccc | 300 |
| ctgataaagc agttccctgt aacctgtgag actggaccag ggagcccctc tggccatgcc | 360 |
| atgggcacag caggtgtata ctacgtgatg gtcacatcta ctctttccat ctttcaggga | 420 |
| aagataaagc cgacctacag atttcggtgc ttgaatgtca ttttgtggtt gggattctgg | 480 |
| gctgtgcagc tgaatgtctg tctgtcacga atctaccttg ctgctcattt tcctcatcaa | 540 |
| gttgttgctg gagtcctgtc aggcattgct gttgcagaaa cttttcagcca catccacagc | 600 |
| atctataatg ccagcctcaa gaaatatttt ctcattacct tcttcctgtt cagcttcgcc | 660 |
| atcggatttt atctgctgct caagggactg gtgtagacc tcctgtggac tctggagaaa | 720 |
| gcccagaggt ggtgcgagca gccagaatgg gtccacattg acaccacacc ctttgccagc | 780 |
| ctcctcaaga acctgggcac gctctttggc ctggggctgg ctctcaactc cagcatgtac | 840 |
| agggagagct gcaaggggaa actcagcaag tggctcccat tccgcctcag ctctattgta | 900 |
| gcctccctcg tcctcctgca cgtctttgac tccttgaaac ccccatccca agtcgagctg | 960 |
| gtcttctacg tcttgtcctt ctgcaagagt gcggtagtgc cctggcatc cgtcagtgtc | 1020 |
| atcccctact gcctcgccca ggtcctgggc cagccgcaca agaagtcgtt gtaa | 1074 |

<210> SEQ ID NO 5
<211> LENGTH: 91
<212> TYPE: DNA
<213> ORGANISM: Homo sapiens

<400> SEQUENCE: 5

| | |
|---|---:|
| gcattgctgt tgcagaaaact ttcagccaca tccacagcat ctataatgcc agcctcaaga | 60 | aatatttct cattaccttc ttcctttca g 91

<210> SEQ ID NO 6
<211> LENGTH: 357
<212> TYPE: PRT
<213> ORGANISM: Homo sapiens

<400> SEQUENCE: 6

```
Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355
```

<210> SEQ ID NO 7
<211> LENGTH: 25
<212> TYPE: DNA
<213> ORGANISM: Homo sapiens

<400> SEQUENCE: 7
tctcattacc ttcttccttt tcagc                                    25

<210> SEQ ID NO 8
<211> LENGTH: 104
<212> TYPE: DNA
<213> ORGANISM: Homo sapiens

<400> SEQUENCE: 8
gcatctataa tgccagcctc aagaaatatt ttctcattac cttcttcctk ttcagcttcg    60
ccatcggatt ttatctgctg ctcaagggac tgggtgtaga cctc                   104

<210> SEQ ID NO 9
<211> LENGTH: 25
<212> TYPE: DNA
<213> ORGANISM: Artificial Sequence
<220> FEATURE:
<223> OTHER INFORMATION: Control Antisense Oligonucleotide

<400> SEQUENCE: 9
cctcttacct cagttacaat ttata                                    25

<210> SEQ ID NO 10
<211> LENGTH: 21
<212> TYPE: DNA
<213> ORGANISM: Artificial Sequence
<220> FEATURE:
<223> OTHER INFORMATION: Forward primer for First PCR

<400> SEQUENCE: 10
ggtgtatact acgtgatggt c                                        21

<210> SEQ ID NO 11
<211> LENGTH: 20
<212> TYPE: DNA
<213> ORGANISM: Artificial Sequence
<220> FEATURE:
<223> OTHER INFORMATION: Forward primer for Second PCR

<400> SEQUENCE: 11
ttgggattct gggctgtgca                                          20

<210> SEQ ID NO 12
<211> LENGTH: 20
<212> TYPE: DNA
<213> ORGANISM: Artificial Sequence
<220> FEATURE:
<223> OTHER INFORMATION: Reverese primer for First/Second PCR

<400> SEQUENCE: 12
aagggtgtgg tgtcaatgtg                                          20

<210> SEQ ID NO 13
<211> LENGTH: 4169
<212> TYPE: DNA
<213> ORGANISM: Homo sapiens

<400> SEQUENCE: 13

-continued

| | |
|---|---|
| atagcagagc aatcaccacc aagcctggaa taactgcaag ggctctgctg acatcttcct | 60 |
| gaggtgccaa ggaaatgagg atggaggaag gaatgaatgt tctccatgac tttgggatcc | 120 |
| agtcaacaca ttacctccag gtgaattacc aagactccca ggactggttc atcttggtgt | 180 |
| ccgtgatcgc agacctcagg aatgccttct acgtcctctt ccccatctgg ttccatcttc | 240 |
| aggaagctgt gggcattaaa ctcctttggg tagctgtgat tggagactgg ctcaacctcg | 300 |
| tctttaagtg gattctcttt ggacagcgtc catactggtg ggttttggat actgactact | 360 |
| acagcaacac ttccgtgccc ctgataaagc agttccctgt aacctgtgag actggaccag | 420 |
| ggagcccctc tggccatgcc atgggcacag caggtgtata ctacgtgatg gtcacatcta | 480 |
| ctctttccat ctttcaggga aagataaagc cgacctacag atttcggtgc ttgaatgtca | 540 |
| ttttgtggtt gggattctgg gctgtgcagc tgaatgtctg tctgtcacga atctaccttg | 600 |
| ctgctcattt tcctcatcaa gttgttgctg gagtcctgtc aggcattgct gttgcagaaa | 660 |
| ctttcagcca catccacagc atctataatg ccagcctcaa gaaatatttt ctcattacct | 720 |
| tcttcctgtt cagcttcgcc atcggatttt atctgctgct caagggactg ggtgtagacc | 780 |
| tcctgtggac tctggagaaa gcccagaggt ggtgcgagca gccagaatgg gtccacattg | 840 |
| acaccacacc ctttgccagc ctcctcaaga acctgggcac gctctttggc ctggggctgg | 900 |
| ctctcaactc cagcatgtac agggagagct gcaaggggaa actcagcaag tggctcccat | 960 |
| tccgcctcag ctctattgta gcctccctcg tcctcctgca cgtctttgac tccttgaaac | 1020 |
| ccccatccca agtcgagctg gtcttctacg tcttgtcctt ctgcaagagt gcggtagtgc | 1080 |
| ccctggcatc cgtcagtgtc atcccctact gcctcgccca ggtcctgggc cagccgcaca | 1140 |
| agaagtcgtt gtaagagatg tggagtcttc ggtgtttaaa gtcaacaacc atgccaggga | 1200 |
| ttgaggagga ctactatttg aagcaatggg cactggtatt tggagcaagt gacatgccat | 1260 |
| ccattctgcc gtcgtggaat taaatcacgg atggcagatt ggagggtcgc ctggcttatt | 1320 |
| cccatgtgtg actccagcct gccctcagca cagactcttt cagatggagg tgccatatca | 1380 |
| cgtacaccat atgcaagttt cccgccagga ggtcctcctc tctctacttg aatactctca | 1440 |
| caagtaggga gctcactccc actgaacag cccattttat ctttgaatgg tcttctgcca | 1500 |
| gcccattttg aggccagagg tgctgtcagc tcaggtggtc ctcttttaca atcctaatca | 1560 |
| tattgggtaa tgttttttgaa aagctaatga agctattgag aaagaccgt tgctagaagt | 1620 |
| tgggttgttc tggattttcc cctgaagact tacttattct tccgtcacat atacaaaagc | 1680 |
| aagacttcca ggtagggcca gctcacaagc ccaggctgga gatcctaact gagaattttc | 1740 |
| tacctgtgtt cattcttacc gagaaaagga gaaaggagct ctgaatctga taggaaaaga | 1800 |
| aggctgccta aggaggagtt tttagtatgt ggcgtatcat gcaagtgcta tgccaagcca | 1860 |
| tgtctaaatg gctttaatta tatagtaatg cactctcagt aatgggggac cagcttaagt | 1920 |
| ataattaata gatggttagt ggggtaattc tgcttctagt attttttta ctgtgcatac | 1980 |
| atgttcatcg tatttccttg gatttctgaa tggctgcagt gacccagata ttgcactagg | 2040 |
| tcaaaacatt caggtatagc tgacatctcc tctatcacat tacatcatcc tccttataag | 2100 |
| cccagctctg cttttttccag attcttccac tggctccaca tccaccccac tggatcttca | 2160 |
| gaaggctaga gggcgactct ggtggtgctt ttgtatgttt caattaggct ctgaaatctt | 2220 |
| gggcaaaatg acaaggggag ggccaggatt cctctctcag gtcactccag tgttactttt | 2280 |
| aattcctaga gggtaaatat gactcctttc tctatcccaa gccaaccaag agcacattct | 2340 |
| taaaggaaaa gtcaacatct tctctctttt tttttttttt tgagacaggg tctcactatg | 2400 |

-continued

```
ttgcccaggc tgctcttgaa ttcctgggct caagcagtcc tcccacccta ccacagcgtc    2460
ccgcgtagct gggactacag gtgcaagcca ctatgtccag ctagccaact cctccttgcc    2520
tgcttttctt ttttttttctt tttttgagac ggcgcaccta tcacccaggc tggagtggag   2580
tggcacgatc ttggctcact gcaacctctt cctcctggtt caagcgattc tcatgtctca    2640
gcctcctcag tagctaggac taccggcgtg caccaccatg ccaggctaat ttttatattt    2700 ttagaattt agaagagatg ggatttcatc atgttggcca ggctggtctc gaactcctga     2760
cctcaagtga tccacctgcc ttggcctccc aaggtgctag gattacaggc atgagccacc    2820
gcaccgggcc ctccttgcct gttttcaat ctcatctgat atgcagagta tttctgcccc     2880
acccacctac cccccaaaaa aagctgaagc ctatttattt gaaagtcctt gttttgcta    2940 ctaattatat agtataccat acattatcat tcaaaacaac catcctgctc ataacatctt    3000
tgaaaagaaa aatatatatg tgcagtattt tattaaagca acattttatt taagaataaa   3060
gtcttgttaa ttactatatt ttagatgcaa tgtgatctga agtttctaat tctggcccaa   3120
ctaaatttct agctctgttt ccctaaacaa ataatttggt ttctctgtgc ctgcattttc    3180
cctttggaga agaaaagtgc tctctcttga gttgaccgag agtcccatta gggatagga    3240 gacttaaatg catccacagg ggcacaggca gagttgagca cataaacgga ggcccaaaat    3300
cagcatagaa ccagaaagat tcagagttgg ccaagaatga acattggcta ccagaccaca   3360
agtcagcatg agttgctcta tggcatcaaa ttgcaacttg agagtagatg ggcagggtca   3420
ctatcaaatt aagcaatcag ggcacacaag ttgcagtaac acaacaagac taggccagct   3480
ctggaatcca gtaactcagt gtcagcaagg ttttgggtta tagttcaaga aagtctaaac   3540
agagccagtc acagcaccaa ggaatgctca agggagctat tgcaggtttc tctgctaaga   3600
gatttatttc atcctgggtg caggtttcga cctccaaagg cctcaaatca tcaccgtatc   3660
aatggatttc ctgagggtaa gctccgctat ttcacacctg aactccggag tctgtatatt    3720
cagggaagat tgcattctcc tactggattt gggctctcag agggcgttgt gggaaccagg    3780
cccctcacag aatcaaatgg tcccaaccag ggagaaagaa aatagtcttt ttttttttt     3840 taatagagat gggggtctca ctatgctgcc caggctggtc ttgaactcct gggttcaagt    3900
gatcctcctg cctcagcctc ccaaagtgct gggattacag tgtgagccac tgcgcttggc   3960
cagaaatggt tttgatctgt ctgaactgaa ccctactgct taggcatagc ccatccttg    4020 ataatctatt tgctcccaag gaccaagtcc aagatcctta caagaaaggt ctgccagaaa    4080
gtaaatactg cccccactcc ctgaagttta tgaggttgat aagaaaacat aacagataaa    4140
gtttattgag tgctaacttt aaaaaaaaa                                      4169
```

<210> SEQ ID NO 14
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 14
gctgaaaagg aagaaggtaa tgaga                                          25

<210> SEQ ID NO 15
<211> LENGTH: 104
<212> TYPE: DNA
<213> ORGANISM: Artificial Sequence
<220> FEATURE:

<223> OTHER INFORMATION: Antisense Oligonucleotide

<400> SEQUENCE: 15
gaggtctaca cccagtccct tgagcagcag ataaaatccg atggcgaagc tgaamaggaa    60
gaaggtaatg agaaaatatt tcttgaggct ggcattatag atgc    104

<210> SEQ ID NO 16
<211> LENGTH: 28
<212> TYPE: DNA
<213> ORGANISM: Artificial Sequence
<220> FEATURE:
<223> OTHER INFORMATION: Antisense Oligonucleotide

<400> SEQUENCE: 16
tccgatggcg aagctgaaaa ggaagaag    28

<210> SEQ ID NO 17
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 17
ctgaaaagga agaag    15

<210> SEQ ID NO 18
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 18
agctgaaaag gaaga    15

<210> SEQ ID NO 19
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 19
gaagctgaaa aggaa    15

<210> SEQ ID NO 20
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 20
gcgaagctga aaagg    15

<210> SEQ ID NO 21
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 21
tggcgaagct gaaaa    15

<210> SEQ ID NO 22
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 22
gatggcgaag ctgaa                                                    15

<210> SEQ ID NO 23
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 23
ccgatggcga agctg                                                    15

<210> SEQ ID NO 24
<211> LENGTH: 16
<212> TYPE: DNA
<213> ORGANISM: Homo sapiens

<400> SEQUENCE: 24
ccttcttcct tttcag                                                   16

<210> SEQ ID NO 25
<211> LENGTH: 16
<212> TYPE: DNA
<213> ORGANISM: Homo sapiens

<400> SEQUENCE: 25
ccttcttcct gttcag                                                   16

<210> SEQ ID NO 26
<211> LENGTH: 15
<212> TYPE: DNA
<213> ORGANISM: Homo sapiens

<400> SEQUENCE: 26
ctttcttcca ctcag                                                    15

<210> SEQ ID NO 27
<211> LENGTH: 9
<212> TYPE: DNA
<213> ORGANISM: Homo sapiens

<400> SEQUENCE: 27 caggtatgg                                                            9

<210> SEQ ID NO 28
<211> LENGTH: 22
<212> TYPE: DNA
<213> ORGANISM: Homo sapiens

<400> SEQUENCE: 28
gctttcttcc actcaggcat tg                                            22

<210> SEQ ID NO 29
<211> LENGTH: 30
<212> TYPE: DNA

```
<213> ORGANISM: Homo sapiens

<400> SEQUENCE: 29
tctcattacc ttcttccttt tcagcttcgc                                              30
```

ANTISENSE OLIGONUCLEOTIDE AND COMPOSITION FOR PREVENTION OR TREATMENT OF GLYCOGEN STORAGE DISEASE TYPE Ia

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 46,000 Byte ASCII (Text) file named "37837-251_ST25," created on Oct. 2, 2020.

TECHNICAL FIELD

The present invention relates to an antisense oligonucleotide and a composition for preventing or treating glycogen storage disease type Ia.

BACKGROUND ART

Glycogen storage disease type Ia is a disease involving an inherited metabolic disorder caused due to decrease in function of an enzyme "glucose-6-phosphatase (G6Pase)" that catalyzes the last step of an endogenous blood sugar supply route. The glycogen storage disease type Ia is mainly treated by a dietary therapy with frequent intake of starches in combination with a citric acid formulation with respect to acidosis, a uric acid synthesis inhibitor with respect to hyperuricemia, and/or the like. However, such a therapy is far from correction of various abnormal findings due to metabolic disorders, and a long-term progress of the disease state may lead to occurrence of hepatoma and renal failure. For the case of hepatoma, liver transplantation is selected and, for the case of renal failure, renal transplantation is selected (see Non-patent Literature 1).

It is known that, in approximately 90% of Japanese patients affected by glycogen storage disease type Ia, a common variation (i.e., c.648G>T) occurs in G6PC that is a responsible gene of the disease and encodes G6Pase. Specifically, in the common variation, guanine (G) that is a base at position 648 in the coding region DNA is substituted by thymine (T) (Non-patent Literature 2). Although this variation does not cause amino acid substitution, a neighbor sequence of the variation becomes an ectopic splice acceptor site in which aberrant splicing occurs. As a result, a transcript in which 91 base pairs have been deleted is generated (Non-patent Literature 3). In recent years, in regard to the splicing variation, a technique is known which restores normal transcription by a nucleic acid derivative "antisense oligonucleotide (ASO)" which is complementary to a base sequence in that region near the variation (Non-patent Literature 4).

CITATION LIST

Non-Patent Literature

[Non-Patent Literature 1]
Chou J Y et al., J Inherit Metab Dis 38: 511-519, 2014.
[Non-Patent Literature 2]
Akanuma J et al., Am J Med Genet 91: 107-12, 2000.
[Non-Patent Literature 3]
Kajihara S et al., Am J Hum Genet 57: 549-55, 1995.
[Non-Patent Literature 4]
Havens M A et al., WIREs RNA 4: 247-66, 2013.

SUMMARY OF INVENTION

Technical Problem

To date, there is no therapeutic agent specific to glycogen storage disease type Ia. The present invention is accomplished in view of the above problem, and its object is to provide a novel antisense oligonucleotide and a composition for preventing or treating glycogen storage disease type Ia.

Solution to Problem

In order to attain the object, the inventors of the present invention have diligently studied, and found that aberrant splicing of pre-mRNA of c.648G>T variant G6PC is inhibited and a gene transcript which has a normal base length is generated by adding, to cells of a patient affected by glycogen storage disease type Ia, an antisense oligonucleotide that targets a pre-mRNA sequence of the c.648G>T variant G6PC gene. Based on this fining, the present invention has been accomplished. That is, the present invention encompasses any one of the following aspects:

<1> An antisense oligonucleotide which hybridizes with a pre-mRNA sequence derived from a region including at least one of a base at position 42911000, a base at position 42911004, and a base at position 42911005 in a base sequence of human chromosome 17 of GRCh38/hg38 and has activity to inhibit aberrant splicing of pre-mRNA of c.648G>T variant G6PC.

<2> A composition for preventing or treating glycogen storage disease type Ia, the composition including: an antisense oligonucleotide as an active ingredient, the antisense oligonucleotide hybridizing with a pre-mRNA sequence derived from a region including at least one of a base at position 42911000, a base at position 42911004, and a base at position 42911005 in a base sequence of human chromosome 17 of GRCh38/hg38 and having activity to inhibit aberrant splicing of pre-mRNA of c.648G>T variant G6PC.

Advantageous Effects of Invention

The present invention provides a novel antisense oligonucleotide and a composition which is for preventing or treating glycogen storage disease type Ia and contains the antisense oligonucleotide as an active ingredient. The present invention is effective for prevention or treatment of glycogen storage disease type Ia.

DESCRIPTION OF EMBODIMENTS

Figure 1:
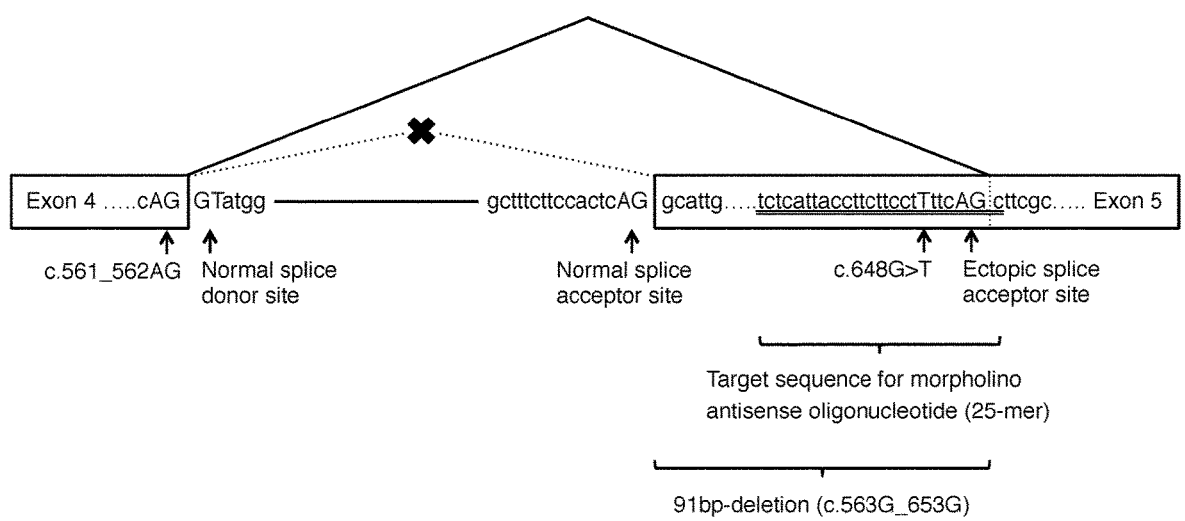
FIG. 1 is a view illustrating an aberrant splicing region in pre-mRNA of G6PC, which is caused by c.648G>T variation (correspondences between the sequences and SEQ ID NOs in FIG. 1 are as follows: cAGGTatgg: SEQ ID NO: 27, gctttcttccactcAGgcattg: SEQ ID NO: 28, tctcattaccttcttcctTttcAGcttcgc: SEQ ID NO: 29)".

The following description will discuss embodiments of the present invention in detail.

Explanations of Terms

"Glucose-6-phosphatase (G6Pase)" catalyzes hydrolysis from glucose-6-phosphate (G6P) to glucose and phosphate in the last step of gluconeogenesis and glycogenolysis, and is an enzyme protein that is important for maintenance of glucose homeostasis. "G6PC" is a gene (locus 17q21) that encodes G6Pase.

"Glycogen storage disease (hereinafter also referred to as "GSD")" is a disease in which synthesis or decomposition of glycogen is inhibited by gene aberrancy in an enzyme or a transporter on a glycogen metabolic pathway. As GSD, 11 types are known. Due to mutation of a G6PC gene, glycogen storage disease type Ia (GSD-Ia) is caused.

"Glycogen storage disease type Ia (also referred to as "GSD-Ia")" is a representative glycogen storage disease, and a rate of incidence thereof is approximately 1 per 100,000 births. GSD-Ia is also known by the alias of von Gierke's disease. GSD-Ia is a genetic disease that is caused due to a congenital defect of G6Pase. Glycogen storage disease type Ia is caused by a homozygous or compound heterozygous variant in the responsible gene.

In GSD-Ia, due to a defect of G6Pase, an ability of a liver to produce free glucose from glycogen and from gluconeogenesis is deteriorated. GSD-Ia is characterized by severe fasting hypoglycemia caused by accumulation of glycogen and fat in a liver and kidneys. Excessive amounts of glucose-6-phosphate generated from glycogen and gluconeogenic precursors do not yield any glucose but run into the glycolytic pathway, resulting in the secondary elevation of lactic acid, uric acid, cholesterol and triglyceride in the blood. The responsible gene G6PC expresses in the liver, kidneys and small intestine, and therefore accumulation of glycogen causes chronic damage to these organs. As such, patients affected by GSD-Ia cannot maintain glucose homeostasis, and show recurrent hypoglycemia, chronic lactic acidosis, growth failure, hepatopathy, nephromegaly, hyperlipemia, hyperuricemia, hepatomegaly, continuous elevation of aminotransferase in the blood, glomerular hyperfiltration, and the like. These symptoms often lead to multiple adenomas in the liver, proteinuria, and in the worst case, malignant liver tumors and chronic renal failure.

In this specification, "protein" is equivalent to "polypeptide". "Protein" includes a structure constituted by peptide bonding of amino acids, and can further include, for example, a structure such as a sugar chain or an isoprenoid group. Unless otherwise noted, "protein" encompasses a polypeptide that contains a known analogue of native amino acid and can function in a manner similar to the native amino acid.

In this specification, "nucleic acid" encompasses polynucleotides constituted by arbitrary simple nucleotides and/or modified nucleotides. Examples of such polynucleotides include cDNA, mRNA, total RNA, hnRNA, and the like.

In this specification, "gene" is interchangeably used with "polynucleotide", "nucleic acid", or "nucleic acid molecule". "Polynucleotide" means a polymer of nucleotides. Therefore, the term "gene" in this specification encompasses not only double strand DNA but also single strand (such as sense strand and antisense strand) DNA and RNA (such as mRNA) which constitute the double strand DNA.

In this specification, "oligonucleotide" means a polymer of a predetermined number of nucleotides. In this specification, a length of "oligonucleotide" is not limited. Note, however, that it is intended that "oligonucleotide" is "polynucleotide" having a relatively short nucleotide chain.

"Antisense oligonucleotide (also referred to as "ASO")" is a generic term of oligonucleotide that hybridizes with a target nucleic acid sequence (corresponding to sense sequence) so as to adjust expression of a target gene which is encoded by a nucleic acid sequence including the target nucleic acid sequence.

In this specification, "DNA" encompasses cDNA, genomic DNA, and the like which can be obtained by, for example, cloning, a chemosynthesis technique, or a combination of those techniques. That is, DNA can be "genomic" DNA including a non-coding sequence such as an intron which is a form included in an animal genome. Alternatively, DNA can be cDNA which is obtained via mRNA with use of reverse transcriptase or polymerase, that is, DNA can be "transcriptive" DNA that does not include a non-coding sequence such as an intron.

"Pre-mRNA" is also referred to as "mRNA precursor", and indicates RNA which includes both exons and introns. "mRNA" indicates RNA in which introns are deleted and exons are bound together. The mRNA is translated into protein.

In this specification, "target sequence" is a portion of target nucleic acid sequence with which the antisense oligonucleotide hybridizes, that is, a sequence with which the antisense oligonucleotide complementarily hybridizes.

In this specification, "prevention" indicates preventing one from being affected by illness, disease, or disorder. "Treatment" indicates easing or removing illness, disease, or disorder from which one is already suffering, or easing or removing symptoms of such illness, disease, or disorder.

In this specification, "healthy" indicates that one is not affected by glycogen storage disease type Ia. Moreover, in this specification, "healthy" encompasses also a case in which one has a risk of being affected by glycogen storage disease type Ia due to, for example, a defect of G6Pase but a clinical symptom has not been developed.

1. Antisense Oligonucleotide

In recent years, a gene therapy with use of antisense oligonucleotide is being established as a selective method that is effective for correcting certain types of genetic defects. The aberrant splicing of mRNA can be a good target for ASO therapy (see Reference Literature 1).

The present invention provides an antisense oligonucleotide which hybridizes with a pre-mRNA sequence derived from a region including at least one of a base at position 42911000, a base at position 42911004, and a base at position 42911005 in a base sequence of human chromosome 17 of GRCh38/hg38 and has activity to inhibit aberrant splicing of pre-mRNA of c.648G>T variant G6PC.

In regard to glycogen storage disease type Ia, it is reported that a variant (c.648G>T) in which a base at position 648, i.e., G (guanine) in a coding region DNA of G6PC is substituted by T (thymine) is a prevalent variant that is specifically found in East Asian countries such as Japan, South Korea, Taiwan, and mainland China (see Reference Literature 2).

This variant, formerly known as 727G>T, does not cause amino acid change. However, this variant activates a sequence (c.652_653AG) from a base which is adenine (A) at position 652 to a base which is guanine (G) at position 653 as an ectopic splice acceptor site in the coding region DNA of G6PC, and this results in 91 bp deletion (SEQ ID NO: 5) from G at position 563 (i.e., c.563G; hereinafter this notation will be employed) to c.653G of exon 5 (see FIG. 1 of Example). As such, in a case where a mutation exists which influences a splicing mechanism of pre-mRNA, the mutation causes aberrant splicing in pre-mRNA, and thus aberrant mRNA or a mRNA fragment is generated which is different from mRNA that is generated from normal pre-mRNA. As a result, production of a normal G6Pase transcript is inhibited.

Specifically, in c.648G>T variant G6PC which is a variant G6PC gene, 2 bases on the 3' side of guanine (c.562G in cDNA (SEQ ID NO: 4)) at position 42909418 in the base sequence of human chromosome 17 of GRCh38/hg38, i.e., guanine (G) at position 42909419 (c.562+1G in cDNA (SEQ ID NO: 4)) and thymine (T) at position 42909420 (c.562+2T in cDNA (SEQ ID NO: 4)) serve as a splice donor site, and 2 bases on the 5' side of cytosine (C) at position 42911006 (c.654C in cDNA (SEQ ID NO: 4)), i.e., adenine (A) at position 42911004 (c.652A in cDNA (SEQ ID NO: 4)) and guanine (G) at position 42911005 (c.653G in cDNA (SEQ ID NO: 4)) serve as a new splice acceptor site (i.e., ectopic splice acceptor site). That is, in c.648G>T variant G6PC, aberrant splicing occurs in which guanine at position 42909419 through guanine at position 42911005 are recognized as an intron, and cytosine at position 42911006 through adenine at position 42914433 are recognized as an exon in the base sequence of human chromosome 17 of GRCh38/hg38. Therefore, in a case where the aberrant splicing that uses the splice donor site constituted by guanine (G) at position 42909419 (c.562+1G in cDNA (SEQ ID NO: 4)) and thymine (T) at position 42909420 (c.562+2T in cDNA (SEQ ID NO: 4)) and the splice acceptor site constituted by adenine (A) at position 42911004 (c.652A in cDNA (SEQ ID NO: 4)) and guanine (G) at position 42911005 (c.653G in cDNA (SEQ ID NO: 4)) is inhibited, an amount of expressed aberrant mRNA is reduced and simultaneously expression of G6PC mRNA having a normal base length based on normal splicing is restored, and this results in restoration of generation of normal G6Pase protein. That is, the phrase "has activity to inhibit aberrant splicing of pre-mRNA of c.648G>T variant G6PC" intends to have at least any of functions to inhibit the aberrant splicing and consequently reduce an amount of expressed aberrant mRNA, to restore expression of G6PC mRNA having a normal base length based on normal splicing, and to generate normal G6Pase protein.

Information of the base sequence of G6PC and the amino acid sequence of G6Pase protein can be obtained, for example, from NCBI Reference Sequence (RefSeq) and GenBank. For example, the G6Pase protein can have, specifically, an amino acid sequence (RefSeq accession number: NP_000142.2) of human G6Pase protein having an amino acid sequence shown in SEQ ID NO: 6.

Here, GRCh38/hg38 is a human genome data assembly (RefSeq assembly accession: GCF_000001405.36, GenBank assembly accession: GCA_000001405.25) registered in https://www.ncbi.nlm.nih.gov/ and the like, and a human chromosome 17 region is indicated by GenBank accession number: CM000679.2.

SEQ ID NO: 1 represents a base sequence of genomic DNA in a base sequence of a G6PC region of human chromosome 17. This sequence is indicated by RefSeq accession number: NG_011808.1. Moreover, the base sequence of genomic DNA of c.648G>T variant G6PC is a sequence in which a base at position 42911000 of the base sequence of human chromosome 17 of GRCh38/hg38 is changed from G to T.

Note that the base at position 42911000 of the base sequence of human chromosome 17 of GRCh38/hg38 corresponds to a base at position 15203 of SEQ ID NO: 1, a base at position 694 of SEQ ID NO: 2 or 3, a base at position 648 of SEQ ID NO: 4, and a base at position 728 of SEQ ID NO: 13. The base at position 42911004 of the base sequence of human chromosome 17 of GRCh38/hg38 corresponds to a base at position 15207 of SEQ ID NO: 1, a base at position 698 of SEQ ID NO: 2 or 3, a base at position 652 of SEQ ID NO: 4, and a base at position 732 of SEQ ID NO: 13. The base at position 42911005 of the base sequence of human chromosome 17 of GRCh38/hg38 corresponds to a base at position 15208 of SEQ ID NO: 1, a base at position 699 of SEQ ID NO: 2 or 3, a base at position 653 of SEQ ID NO: 4, and a base at position 733 of SEQ ID NO: 13.

A base sequence of G6PC mRNA is indicated by RefSeq accession number: NM_000151.3 (SEQ ID NO: 13). A base sequence of a coding region of G6PC is indicated by GenBank accession number: BC130478.1 (SEQ ID NO: 2) and BC136369.1 (SEQ ID NO: 3). Note that the sequence shown in SEQ ID NO: 2 of BC130478.1 is substantially identical with the sequence of BC136369.1 (SEQ ID NO: 3) except that 1 base T is inserted between T at position 2349 and G at position 2350 of the sequence of BC136369.1 (SEQ ID NO: 3).

The antisense oligonucleotide can be a part of a base sequence that encodes the variant G6PC gene. For example, the antisense oligonucleotide can be designed based on a base sequence of genomic DNA, cDNA, pre-mRNA, or mRNA of normal G6PC or c.648G>T variant G6PC. The antisense oligonucleotide in accordance with an aspect of the present invention hybridizes with a pre-mRNA molecule and generates a double strand molecule in a condition in which splicing can be carried out. That is, the antisense nucleotide in accordance with an aspect of the present invention inhibits the aberrant splicing of pre-mRNA which is a primary transcript and restores normal splicing reaction at a transcriptional phase of c.648G>T variant G6PC gene. From this, it is possible to cause G6PC mRNA having a normal base length to express, and thus restore generation of normal G6Pase protein.

The present invention also encompasses an antisense oligonucleotide which (i) hybridizes with a pre-mRNA sequence derived from a region including at least one of bases and single nucleotide polymorphisms which are in a base sequence of human chromosome 17 different from the base sequence of human chromosome 17 of GRCh38/hg38 and correspond to (or are equivalent to) the base at position 42911000, the base at position 42911004, and the base at position 42911005 in the base sequence of human chromosome 17 of GRCh38/hg38 and (ii) has activity to inhibit aberrant splicing of pre-mRNA of c.648G>T variant G6PC. Here, "bases and single nucleotide polymorphisms which correspond to (or are equivalent to)" means bases and single nucleotide polymorphisms of a base sequence of human chromosome 17 that is different from the base sequence of human chromosome 17 of GRCh38/hg38. This accordingly means that a base sequence of human chromosome 17 and the like which are slightly changed depending on differences between human individuals are also encompassed in the target sequence.

A specific sequence of the antisense nucleotide can be a sequence that targets a surrounding sequence of the ectopic splice acceptor site used for the aberrant splicing. In an embodiment, the antisense nucleotide can be an antisense nucleotide that hybridizes with a pre-mRNA sequence of a sequence included in a region constituted by 50 bases upstream of and 50 bases downstream of at least one of the base at position 42911000, the base at position 42911004, and the base at position 42911005 in the base sequence of human chromosome 17 of GRCh38/hg38. In other words, the antisense oligonucleotide in accordance with an embodiment is an antisense oligonucleotide which hybridizes with a pre-mRNA sequence derived from a region including bases at positions 42910951 to 42911054 (c.599G to c.702C of cDNA (SEQ ID NO: 4)) in the base sequence of human chromosome 17 of GRCh38/hg38 and has activity to inhibit aberrant splicing of pre-mRNA of c.648G>T variant G6PC. In another embodiment, the antisense nucleotide can be an antisense nucleotide that hybridizes with a pre-mRNA sequence of a sequence included in a region constituted by 30 bases upstream of and 30 bases downstream of at least one of the base at position 42911000, the base at position 42911004, and the base at position 42911005 in the base sequence of human chromosome 17 of GRCh38/hg38. In other words, the antisense oligonucleotide in accordance with another embodiment is an antisense oligonucleotide which hybridizes with a pre-mRNA sequence derived from a region including bases at positions 42910971 to 42911034 (c.619A to c.682A of cDNA (SEQ ID NO: 4)) in the base sequence of human chromosome 17 of GRCh38/hg38 and has activity to inhibit aberrant splicing of pre-mRNA of c.648G>T variant G6PC.

An antisense oligonucleotide in accordance with a certain embodiment is an antisense oligonucleotide which hybridizes with a pre-mRNA sequence derived from a region including one, two, or three (i.e., all) of the base at position 42911000, the base at position 42911004, and the base at position 42911005 in the base sequence of human chromosome 17 of GRCh38/hg38 and has activity to inhibit aberrant splicing of pre-mRNA of c.648G>T variant G6PC.

A sequence of the antisense oligonucleotide in accordance with an aspect of the present invention is selected so as to block an ectopic splice acceptor site that is a factor causing aberrant splicing.

In a case where the antisense nucleotide is used, a normal intron region is removed by normal splicing, and mRNA that encodes normal G6Pase protein is produced. The antisense oligonucleotide in accordance with an aspect of the present invention includes a base sequence that can hybridize with the foregoing target sequence, and has activity to inhibit aberrant splicing of pre-mRNA of c.648G>T variant G6PC.

The antisense oligonucleotide in accordance with an embodiment includes a base sequence that is sufficiently complementary to a region that includes an ectopic splice acceptor site of a region in exon 5 of a pre-mRNA sequence of c.648G>T variant G6PC. The antisense oligonucleotide inhibits aberrant splicing of pre-mRNA of c.648G>T variant G6PC, and thus can increase expression of normal G6Pase protein having normal activity. A specific sequence of such an antisense oligonucleotide can be, for example, an oligonucleotide including a base sequence (SEQ ID NO: 14) that hybridizes with SEQ ID NO: 7. The base sequence shown in SEQ ID NO: 7 is a sequence that conforms to positions 630 to 654 in c.648G>T variant of the base sequence (SEQ ID NO: 4) of DNA in the coding region of G6PC.

The antisense oligonucleotide in accordance with an embodiment is specifically an antisense oligonucleotide that is selected from the following (a) through (c).

(a) an antisense oligonucleotide including a base sequence shown in SEQ ID NO: 14;

(b) an antisense oligonucleotide which includes a base sequence in which 1 to 10 bases, preferably 1 to 5 bases are deleted, substituted, inserted, and/or added in the base sequence shown in SEQ ID NO: 14 and has activity to inhibit aberrant splicing of pre-mRNA of c.648G>T variant G6PC;

(c) an antisense oligonucleotide which includes a base sequence having a sequence identity of 60% or higher with respect to the base sequence shown in SEQ ID NO: 14 and has activity to inhibit aberrant splicing of pre-mRNA of c.648G>T variant G6PC. Here, the sequence identity is preferably 65% or higher, more preferably 70% or higher, 75% or higher, 80% or higher, 85% or higher, 90% or higher, particularly preferably 95% or higher, 96% or higher, 97% or higher, 98% or higher, 99% or higher.

The antisense oligonucleotides in the above (b) and (c) can be said to be, specifically, variants of the antisense oligonucleotide of the above (a). That is, this intends that polymorphism between genes in a population and the like are also encompassed.

That is, the antisense nucleotide in accordance with an embodiment is an antisense oligonucleotide that is complementary to a region including single nucleotide polymorphism (SNP) that is represented by rs80356484 (polymorphism of G/T) of pre-mRNA of G6PC, and has activity to inhibit aberrant splicing of pre-mRNA of c.648G>T variant G6PC. The rs number of rs80356484 is a registration number in the dbSNP database (http//www.ncbi.nlm.nih.gov/projects/SNP/) of National Center for Biotechnology Information, and can be obtained from the website (https://www.ncbi.nlm.nih.gov/SNP/snp_ref.cgi?rs=80356484&pt=1ZS1UX0_YR_X1REc5s-B-00w7e7HgeIfXE3I8aMuPnE iTRLgNu).

In regard to rs80356484, SEQ ID NO: 8 represents a sequence (c.599G to c.702C) having a total length of 104 bp including a base (c.648G/T) of SNP, c.652A, c.653G, and regions in front and behind these bases. The base at position 50 has polymorphism.

The antisense oligonucleotide in accordance with another embodiment of the present invention is specifically an antisense oligonucleotide that is selected from the following (d) through (h).

(d) an antisense oligonucleotide which has a base sequence that is wholly or partially represented by a sequence of SEQ ID NO: 15 (that hybridizes with SEQ ID NO: 8) and at least includes all bases at positions 50 to 55 in the sequence of SEQ ID NO: 15;

(e) the antisense oligonucleotide of the above (d) whose sequence length is 7 bases or more, 10 bases or more, 11 bases or more, 12 bases or more, 13 bases or more, 14 bases or more, 15 bases or more, 16 bases or more, 17 bases or more, 18 bases or more, 19 bases or more, 20 bases or more, 21 bases or more, 22 bases or more, 23 bases or more, 24 bases or more, or 25 bases or more;

(f) the antisense oligonucleotide of the above (d) or (e) whose sequence length is 104 bases or less, 103 bases or less, 102 bases or less, 101 bases or less, 100 bases or less, 90 bases or less, 80 bases or less, 70 bases or less, 60 bases or less, 50 bases or less, 40 bases or less, 35 bases or less, 30 bases or less, 29 bases or less, 28 bases or less, 27 bases or less, or 26 bases or less;

(g) an antisense oligonucleotide having a sequence identity of 95% or higher, 96% or higher, 97% or higher, 98% or higher, or 99% or higher, with respect to the antisense oligonucleotide described in any of the above (d) through (f); and (h) the antisense oligonucleotide of any of the above (d) through (g) which preferably satisfies at least one, at least two, or three of conditions A) a base at position 50 of SEQ ID NO: 15 is C, B) a base at position 51 is T, and C) a base at position 55 is A.

Note that hybridization of the antisense oligonucleotide with the target sequence is not limited to a case where the base sequence of the antisense oligonucleotide is completely complementary to a base sequence of the target sequence in a region in which the hybridization can occur. For example, in a case where the region in which the hybridization can occur has 25 bp or more, the antisense oligonucleotide can have a sequence identity of 60% or higher, preferably 65% or higher, 70% or higher, 75% or higher, 80% or higher, more preferably 85% or higher, further preferably 90% or higher, particularly preferably 95% or higher, with respect to a sequence that is completely complementary to a base sequence of pre-mRNA in the region. Alternatively, in a case where the region in which the hybridization can occur has 25 bp or more, the antisense oligonucleotide has a difference of 10 bases or less, preferably 5 bases or less, 4 bases or less, more preferably 3 bases or less, further preferably 2 bases or less, particularly preferably 1 base, with respect to the completely complementary sequence. In another example, in a case where the region in which the hybridization can occur has 7 bp or more, the antisense oligonucleotide can have a difference of preferably 2 bases or less, more preferably 1 base, with respect to a sequence that is completely complementary to a base sequence of pre-mRNA in the region.

The antisense oligonucleotide can be any of DNA molecules, RNA molecules, and hybrid molecules of DNA and RNA. From the viewpoint of stability, the antisense oligonucleotide may be preferably DNA molecules.

A length of the antisense oligonucleotide in accordance with an aspect of the present invention is not particularly limited, and a suitable length may vary depending on modification types of oligonucleotide. An antisense oligonucleotide in accordance with a certain embodiment includes preferably 7 to 104 bases, more preferably 10 to 104 bases, furthermore preferably 15 to 64 bases, particularly preferably 15 to 44 bases, most preferably 15 to 30 bases. As another example, in a case where the antisense oligonucleotide in accordance with an aspect of the present invention is a morpholino oligonucleotide (described later), the antisense oligonucleotide includes preferably 14 to 30 bases, particularly preferably 20 to 30 bases. As still another example, in a case where the antisense oligonucleotide in accordance with an aspect of the present invention is an oligonucleotide including a locked nucleic acid (LNA; later described), that is, in a case where the antisense oligonucleotide is an LNA oligonucleotide, the antisense oligonucleotide includes preferably 7 to 25 bases, more preferably 7 to 23 bases, furthermore preferably 9 to 20 bases, particularly preferably 10 to 17 bases.

The antisense oligonucleotide in accordance with an aspect of the present invention can be a native oligonucleotide or can be a nonnative oligonucleotide. Examples of the nonnative oligonucleotide include oligonucleotides having modified skeletons such as a morpholino skeleton, a carbamate skeleton, a siloxane skeleton, a sulfide skeleton, a sulfoxide skeleton, a sulfone skeleton, a formacetyl skeleton, a thioformacetyl skeleton, a methylene formacetyl skeleton, a riboacetyl skeleton, an alkene-containing skeleton, a sulfomate skeleton, a sulfonate skeleton, a sulfonamide skeleton, a methyleneimino skeleton, a methylene hydrazino skeleton, and an amide skeleton. The nonnative oligonucleotide can be a morpholino oligonucleotide such as a phosphoroamidate morpholino oligonucleotide or a phosphorodiamidate morpholino oligonucleotide (PMO), PMO-X, PPMO, a peptide nucleic acid (PNA), a locked nucleic acid (LNA), a phosphorothioate oligonucleotide, a tricyclo-DNA oligonucleotide, a tricyclo-phosphorothioate oligonucleotide, a 2'O-Me modified oligonucleotide, 2'-O,4'-C-ethylene bridged nucleic acids (ENA), and the like. These nonnative oligonucleotides are not easily decomposed by nuclease and, accordingly, act in cells efficiently. For example, the morpholino oligonucleotide is known to improve stability with respect to nuclease and facilitate intake to cells. The morpholino oligonucleotide has a nucleic acid base that binds to a morpholine ring instead of a deoxyribose ring or a ribose ring. The LNA is known to enhance binding affinity to a target nucleic acid and has a tolerance to nuclease. The LNA oligonucleotide can be produced by substituting one or more nucleotides in a native oligonucleotide by LNA. In a case where the antisense oligonucleotide in accordance with an aspect of the present invention is an LNA oligonucleotide, a preferable ratio of contained LNA per oligonucleotide varies depending on a length of the antisense oligonucleotide. For example, in a case where a length of the LNA oligonucleotide is 10 to 17 bases, it is preferable to contain LNA by preferably 20% to 55%, more preferably 25% to 55%, furthermore preferably 30% to 50%.

Alternatively, for example, in a case where a length of the LNA oligonucleotide is 7 to 9 bases, it is preferable to contain LNA by preferably 40% to 100%, more preferably 50% to 100%, furthermore preferably 70% to 100%.

An antisense oligonucleotide in accordance with a certain embodiment is an antisense oligonucleotide which is selected from the above (d) through (h) and in which nucleotides are partially or wholly LNA. An antisense oligonucleotide in accordance with an embodiment is an antisense oligonucleotide which is selected from the above (d) through (h) and in which nucleotides are LNA at alternate bases. An example is an antisense oligonucleotide which has a length of 15 bases and includes a base sequence shown in SEQ ID NO: 17, 20, or 23, and in which LNAs are introduced at alternative residues, bases on the 3' end and the 5' end are set to native nucleotides, and bases are bound to each other by phosphorothioate.

The 5' end and/or 3' end of the antisense oligonucleotide in accordance with an aspect of the present invention can be modified. Examples of the modification include triethylene glycol (TEG) modification, hexaethylene glycol (HEG) modification, dodecaethylene glycol (DODEG) modification, and the like. Alternatively, the antisense oligonucleotide can have a spacer compound between bases constituting the antisense oligonucleotide. The antisense oligonucleotide can include one or more modified nucleotides, one or more modified or altered linkages between nucleotides, and the like. Examples of the linkage between nucleotides include phosphorothioate (PS) linkage, phosphorodithioate linkage, alkylphosphonate linkage, phosphoroamidate linkage, boranophosphate linkage, and the like.

The antisense oligonucleotide can be obtained by a publicly known genetic engineering technique and a polynucleotide synthesis method. Specifically, the antisense oligonucleotide can be prepared by use of a known method such as chemosynthesis, in vitro transcription, or the like.

(Vector)

The present invention provides also a vector in which the antisense oligonucleotide in accordance with an aspect of the present invention is incorporated so that the antisense oligonucleotide can be expressed. The vector in which an oligonucleotide that encodes the antisense oligonucleotide is incorporated is not particularly limited, and is preferably a vector that is applicable to a gene therapy. Examples of the vector encompass virus vectors such as an adenovirus vector, an adeno-associated virus vector, a herpesvirus vector, a vaccinia virus vector, and a retrovirus vector; a plasmid vector; and the like. The virus vector is preferably altered so as to lack self-replicating ability.

It is preferable that an expression regulatory sequence which causes the antisense oligonucleotide to be expressed specifically in subject cells is incorporated in the vector. Here, the expression regulatory sequence is, for example, a promoter, an enhancer, or the like. Construction of an expression vector can be carried out by use of a publicly known genetic engineering technique.

It is preferable that an expression regulatory sequence which causes the antisense oligonucleotide to be expressed specifically in a target organ of an administration target subject is incorporated in the vector. Here, the expression regulatory sequence is, for example, a promoter, or an enhancer.

(Host Cell)

The present invention provides also a host cell in which a vector including the antisense oligonucleotide in accordance with an aspect of the present invention is introduced. For example, an isolated host cell can be a cell (or cell line) that is suitable for producing a recombinant cell. In some examples, the host cell is mammalian cells such as HEK-293 cell and BHK cell.

2. Method for Inhibiting Aberrant Splicing of Pre-mRNA of c.648G>T Variant G6PC That is, as a certain aspect of the present invention, the antisense oligonucleotide in accordance with the present invention and the composition (later described) including the antisense oligonucleotide in accordance with the present invention can be of course effectively used as an in vitro or in vivo method or as means for molecular biological research for inhibiting aberrant splicing in the c.648G>T variant G6PC gene.

Therefore, the present invention provides also a method for inhibiting aberrant splicing of pre-mRNA of c.648G>T variant G6PC. The method in accordance with an embodiment encompasses inhibiting aberrant splicing of pre-mRNA of c.648G>T variant G6PC by adding the above described antisense oligonucleotide to an in vitro or in vivo cell. This method can further include a step of splicing pre-mRNA, and a step of translating mRNA that has been generated by the splicing of pre-mRNA. Note that an amount of the antisense oligonucleotide added to the in vitro or in vivo cell, a cell culture period after the addition, and the like are set as appropriate in accordance with a type of cell, a purpose, and/or the like.

Whether or not aberrant splicing has been inhibited can be performed by checking base sequences of G6PCmRNA surrounding the splicing region. A method for checking the sequence can be a publicly known sequencing technique such as a direct sequencing method. Alternatively, for example, the sequence can be determined based on a sequence length that has been amplified by use of a publicly known polynucleotide amplification method such as nested PCR.

The inhibition of aberrant splicing and the restoration of expression of G6PC mRNA having a normal base length can be confirmed by, for example, introducing the antisense oligonucleotide in accordance with an aspect of the present invention into a cell (e.g., lymphoblastoid cell) of a subject and carrying out a publicly known mRNA measuring method such as quantitative RT-PCR with respect to the cell as a sample. The restoration of generation of normal G6Pase protein can be confirmed by carrying out a publicly known protein measuring method such as a western blotting method or ELISA with respect to the cell of the subject as a sample. As an expression amount of G6PC mRNA that is generated by normal splicing and has a normal base length is larger, it is expected that an expression amount of normal G6Pase protein is also larger.

3. Composition for Preventing or Treating Glycogen Storage Disease Type Ia

The composition for preventing or treating glycogen storage disease type Ia in accordance with an aspect of the present invention is a composition including: an antisense oligonucleotide as an active ingredient, the antisense oligonucleotide hybridizing with a pre-mRNA sequence derived from a region including at least one of a base at position 42911000, a base at position 42911004, and a base at position 42911005 in a base sequence of human chromosome 17 of GRCh38/hg38 and having activity to inhibit aberrant splicing of pre-mRNA of c.648G>T variant G6PC.

The antisense oligonucleotide that is contained in the composition for prevention or treatment in accordance with an embodiment of the present invention is the antisense oligonucleotide that has been described above in the section [1. Antisense oligonucleotide]. Note that a single composition for preventing or treating glycogen storage disease type Ia can contain two or more types of antisense oligonucleotides. For example, the antisense oligonucleotide that is contained in the composition in accordance with an aspect of the present invention can be contained in a state of the oligonucleotide itself and can be in a form for being administered to a subject. Alternatively, the antisense oligonucleotide can be in a form of being taken into the living body of the subject as an antisense RNA expression vector that is incorporated in a downstream portion of an appropriate promoter sequence.

The composition for preventing or treating glycogen storage disease type Ia in accordance with the present embodiment inhibits aberrant splicing of pre-mRNA of c.648G>T variant G6PC, and it is therefore possible to prevent or treat glycogen storage disease type Ia by administering the composition to a subject. From this, the composition in accordance with the present embodiment is, for example, effective for treatment of a patient affected by glycogen storage disease type Ia. Moreover, the composition in accordance with the present invention can be used in curative or preventive treatment of a subject who has an increasing risk of developing glycogen storage disease type Ia.

The composition for preventing or treating glycogen storage disease type Ia in accordance with an embodiment contains the antisense oligonucleotide which targets the c.648G>T common variation of G6PC. Therefore, it is expected that a pharmacotherapy will be realized which is specific to patients affected by glycogen storage disease type Ia having common variation, that is, to a large number of patients in East Asian countries including Japan as above described.

(Solvent)

Examples of a solvent for the composition for preventing or treating glycogen storage disease type Ia in accordance with an embodiment include water, a buffer solution, and the like. The buffer solution is, specifically, a physiological saline solution, a phosphate buffer, a Ringer's solution, or the like. A solvent that is used for the composition can be a mixture of two or more of the above solvents.

(Other Components)

The composition for preventing or treating glycogen storage disease type Ia in accordance with an embodiment can further contain other components in addition to the antisense oligonucleotide. Those other components are not particularly limited and can be, for example, a pharmaceutically acceptable carrier, a lubricant, a preservative, a stabilizer, a wetting agent, an emulsifier, a buffer, a colorant, a flavoring agent, a sweetener, an antioxidant, a viscosity modifier, and the like. Further, if necessary, a complex drug can be constituted by adding, as an element, a publicly known chemical agent to the composition for preventing or treating glycogen storage disease type Ia in accordance with an aspect of the present invention. It is preferable that the components contained in the composition have a characteristic that the components neither inhibit the function of the antisense oligonucleotide nor give a substantive negative influence on a subject to which the composition is administered.

As those other components, it is possible to use a wide variety of components which are publicly known in this field. Specifically, examples of such components include, but not limited to, lactose, dextrose, cane sugar, sorbitol, mannitol, starch, alcohol, vegetable oil, polyethylene glycol, gelatin, gum arabic, calcium phosphate, calcium silicate, cellulose, talc, hydroxymethyl cellulose, and polyvinylpyrrolidone. A type of the carrier may be selected as appropriate in accordance with a dosage form, an administration method, and the like of the composition.

(Dosage Form)

A dosage form of the composition for preventing or treating glycogen storage disease type Ia is also not limited to a particular one, and can be a liquid or solid, or semi-solid or semi-liquid. Alternatively, the dosage form can be a lyophilized formulation. Examples of the dosage form include a tablet, a pill, powder, a liquid medicine, a suspension, an emulsion, a granule, a capsule, a suppository, an injectable formulation, and the like. The dosage form is preferably the injectable formulation or a dosage form for oral administration such as the tablet.

(Route of Administration)

Examples of a route of administration of the composition for preventing or treating glycogen storage disease type Ia include, but not limited to, oral, local, subcutaneous, intramuscular, intravenous, intradermal, percutaneous, and the like.

(Administration Method)

An administration method of the composition for preventing or treating glycogen storage disease type Ia is not limited to a particular one. The composition can be administered to the whole body by a method such as oral administration, intravascular administration, or enteral administration. Alternatively, the composition can be topically administered by a method such as percutaneous administration or sublingual administration. Administration to a subject can be carried out based on a known method. Specifically, examples of the administration method include direct injections such as a subcutaneous injection, an intravenous injection, an intramuscular injection, an intraabdominal injection, and an intradermal injection, spray to mucous membranes such as a nasal mucosa, an oral mucosa, a lung mucosa, a vaginal mucosa, and a rectal mucosa, oral administration, intravascular administration such as intravenous administration and intraarterial administration, and the like. One preferable administration method is whole body administration by a direct subcutaneous injection, a direct intravenous injection, or a direct intraarterial injection. Another preferable administration method is oral administration, from the viewpoint of easy administration.

(Dosage and Administration Period)

A dosage (therapeutically effective amount) of the composition for preventing or treating glycogen storage disease type Ia can be selected as appropriate in accordance with an age, a body weight, and a gender of an administration target subject, a dosage form for administration, an intended degree of preventive or curative effect on glycogen storage disease type Ia, and the like. Moreover, an administration period of the composition for preventing or treating glycogen storage disease type Ia can also be selected as appropriate so that an intended preventive or curative effect on glycogen storage disease type Ia can be achieved.

For example, as long as the preventive or curative effect on glycogen storage disease type Ia of the composition for preventing or treating glycogen storage disease type Ia is not deteriorated, the composition can be administered in combination with a medicine having another preventive or curative effect on glycogen storage disease type Ia or a medicine having another effect.

(Administration Target)

A subject to which the composition in accordance with an aspect of the present invention is to be administered can be any animal, and is preferably a vertebrate animal, more preferably a mammal. The mammalian subject can be, in addition to human, domestic animals (such as chicken, pig, horse, goat, sheep, and cattle), pet animals (such as cat, dog, hamster, rabbit, and guinea pig), and experimental animals (such as rodents such as mouse and rat, and monkey). Note, however, that the mammalian subject is particularly preferably human. Further, in a case where the subject is human, the subject is preferably an East Asian (such as Japanese, Chinese, Korean, Taiwanese, or the like).

For example, a subject is a patient having glycogen storage disease type Ia or has a risk of developing glycogen storage disease type Ia. According to another embodiment, a subject has c.648G>T variant in a form of homozygote or in a form of compound heterozygote (preferably in homozygosis) in G6PC.

Further, the subject can be of any age. Note that glycogen storage disease type Ia is a disease that can be developed in infancy, and it is therefore preferable to start administration as early as possible including a subject of 0 year old. By starting administration as young as possible, it is possible to prevent growth failure, renal damage, and the like early. Moreover, by early prevention and early start of treatment of the disease, it is possible to prevent severe damage and the like from occurring.

In the subject in accordance with an embodiment, glycogen accumulation is increased in one or more organs including liver, kidneys, and small intestine, or the subject has at least one of the above described clinical symptoms of the glycogen storage disease type Ia.

The composition in accordance with an aspect of the present invention can be easily administered and has high safety. Therefore, the composition can be administered for a long time or can be administered to infants. Therefore, the composition can be suitably used to prevent or treat glycogen storage disease type Ia.

4. Method for Treating Glycogen Storage Disease Type Ia (GSD-Ia)

A method in accordance with an aspect of the present invention for treating glycogen storage disease type Ia includes a step of administering a therapeutically effective amount of the composition for preventing or treating glycogen storage disease type Ia to a subject. In an embodiment, only the composition can be solely administered to the administration target subject. Alternatively, the composition can be administered as a constituent component of a pharmaceutical composition that is suitable for a purpose of administration.

(Dosage and Administration Period)

A dosage (therapeutically effective amount) of the composition for preventing or treating glycogen storage disease type Ia may be set as appropriate in accordance with an age, a gender, and a body weight of an administration target subject, a symptom, a route of administration, the number of administration, an administration period, and the like. The administration method, the dosage, the administration period, and the like are as described in [3. Composition for preventing or treating glycogen storage disease type Ia].

The number of administration of the composition for preventing or treating glycogen storage disease type Ia is also not particularly limited, provided that the curative effect can be brought about. The number of administration can be set as appropriate in accordance with, for example, a severity of disease symptom of the subject, the dosage, a route of administration, a symptom, an age, a gender, and a body weight of the subject, and the like.

Note that the therapeutic method in accordance with an aspect of the present invention also encompasses a preventive administration form which includes a step of administering the composition for preventing or treating glycogen storage disease type Ia to a clinically healthy subject before glycogen storage disease type Ia is developed. That is, the present invention encompasses an aspect in which glycogen storage disease type Ia is prevented by causing a subject to be in a state in which an effective dose or more of the composition is administered in the living body in advance.

(Combination Therapy)

According to the method in accordance with an aspect of the present invention for treating glycogen storage disease type Ia, it is possible to carry out a combination therapy in which the therapeutic method in accordance with an aspect of the present invention is combined with one or more of conventional therapies such as administration of a chemical agent (e.g., a citric acid formulation for acidosis, a uric acid synthesis inhibitor for hyperuricemia, or the like) that is used to treat glycogen storage disease type Ia and is different from the composition for preventing or treating glycogen storage disease type Ia in accordance with the present invention, and a frequent dietary therapy with starches. The method in accordance with an aspect of the present invention for treating glycogen storage disease type Ia is a novel therapeutic method that utilizes a mechanism different from a conventional treatment of glycogen storage disease type Ia. Therefore, by employing this combination therapy, it is possible to expect a synergistic curative effect with a curative effect of the agent used together.

A curative effect on a subject who is being treated with the above therapeutic method can be checked by appropriately using the method for checking whether or not aberrant splicing is inhibited, the method for checking expression of G6PC mRNA having a normal base length, and the method for checking expression of normal G6Pase protein, which are described in [2. Method for inhibiting aberrant splicing of pre-mRNA of c.648G>T variant G6PC]. An amount of G6Pase protein in a living body can be proportional to severity of glycogen storage disease type Ia that the living body has. Therefore, it is possible to check whether or not the curative effect is brought about, at each phase of the treatment.

5. Examples of Specific Aspects of the Present Invention

The present invention encompasses any one of the following aspects:

<1> An antisense oligonucleotide which hybridizes with a pre-mRNA sequence derived from a region including at least one of a base at position 42911000, a base at position 42911004, and a base at position 42911005 in a base sequence of human chromosome 17 of GRCh38/hg38 and has activity to inhibit aberrant splicing of pre-mRNA of c.648G>T variant G6PC.

<2> The antisense oligonucleotide described in <1>, in which the antisense oligonucleotide hybridizes with a pre-mRNA sequence derived from a region including bases at positions 42910951 to 42911054 in the base sequence of human chromosome 17 of GRCh38/hg38 and has activity to inhibit aberrant splicing of pre-mRNA of c.648G>T variant G6PC.

<3> The antisense oligonucleotide describe in <1> or <2>, in which the antisense oligonucleotide is made up of 7 to 104 bases.

<4> The antisense oligonucleotide described in any one of <1> through <3>, in which the antisense oligonucleotide is selected from (a) and (b) below:

(a) an antisense oligonucleotide including a base sequence shown in SEQ ID NO: 14, SEQ ID NO: 17, SEQ ID NO: 20, or SEQ ID NO: 23;

(b) an antisense oligonucleotide which includes a base sequence having a sequence identity of 60% or higher with respect to a base sequence shown in SEQ ID NO: 14, SEQ ID NO: 17, SEQ ID NO: 20, or SEQ ID NO: 23 and has activity to inhibit aberrant splicing of pre-mRNA of c.648G>T variant G6PC.

<5> The antisense oligonucleotide described in any one of <1> through <4>, in which the antisense oligonucleotide is a morpholino antisense oligonucleotide made up of 14 to 30 bases or is a locked nucleic acid (LNA) antisense oligonucleotide made up of 7 to 25 bases.

<6> A composition for preventing or treating glycogen storage disease type Ia, the composition including: an antisense oligonucleotide as an active ingredient, the antisense oligonucleotide hybridizing with a pre-mRNA sequence derived from a region including at least one of a base at position 42911000, a base at position 42911004, and a base at position 42911005 in a base sequence of human chromosome 17 of GRCh38/hg38 and having activity to inhibit aberrant splicing of pre-mRNA of c.648G>T variant G6PC.
<7> The composition described in <6>, in which: the antisense oligonucleotide hybridizes with a pre-mRNA sequence derived from a region including bases at positions 42910951 to 42911054 in the base sequence of human chromosome 17 of GRCh38/hg38 and has activity to inhibit aberrant splicing of pre-mRNA of c.648G>T variant G6PC.
<8> The composition described in <6> or <7>, in which the antisense oligonucleotide is made up of 7 to 104 bases.
<9> The composition described in any one of <6> through <8>, in which the antisense oligonucleotide is selected from (a) and (b) below:
(a) an antisense oligonucleotide including a base sequence shown in SEQ ID NO: 14, SEQ ID NO: 17, SEQ ID NO: 20, or SEQ ID NO: 23;
(b) an antisense oligonucleotide which includes a base sequence having a sequence identity of 60% or higher with respect to a base sequence shown in SEQ ID NO: 14, SEQ ID NO: 17, SEQ ID NO: 20, or SEQ ID NO: 23 and has activity to inhibit aberrant splicing of pre-mRNA of c.648G>T variant G6PC.
<10> The composition described in any one of <6> through <9>, in which the antisense oligonucleotide is a morpholino antisense oligonucleotide made up of 14 to 30 bases or is a locked nucleic acid (LNA) antisense oligonucleotide made up of 7 to 25 bases.

As above described, the present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will discuss Examples of the present invention.

Example 1

First, an aberrant splicing site of pre-mRNA of c.648G>T variant G6PC will be explained with reference to a drawing. FIG. 1 is a view illustrating an aberrant splicing region in pre-mRNA of G6PC, which is caused by c.648G>T variant.

G6PC variant c.648G>T generates mRNA in which 91 bp of nucleotides (SEQ ID NO: 5) on the 5' side of exon 5 are deleted. This may be because an extended polypyrimidine region of a variation sequence "ccttcttcctTttcAG" (SEQ ID NO: 24) has an enhanced splicing effect that exceeds a normal sequence "ccttcttcctGttcAG" (SEQ ID NO: 25) and a sequence of a wild type splice acceptor site "ctttcttcactcAG" (SEQ ID NO: 26). The antisense oligonucleotide was designed to block an ectopic splice acceptor site in a variation sequence in exon 5.
    =Materials and Method=
    (Antisense Oligonucleotide)
A 25-mer morpholino antisense oligonucleotide (mASO) was designed which targeted an ectopic splice acceptor site for aberrant splicing in pre-mRNA of c.648G>T variant G6PC. The mASO which was designed to be a complementary sequence (5'-GCTGAAAAGGAAGAAGGTAAT-GAGA-3' (SEQ ID NO: 14)) to a sequence (5'-TCTCAT-TACCTTCTTCCTTTTCAGC-3' (SEQ ID NO: 7)) from c.630T to c.654C in a G6PC sequence in which c.648G was substituted by c.648T was synthesized with a control morpholino oligonucleotide (mCO) (5'-CCTCTTACCTCAGT-TACAATTTATA-3' (SEQ ID NO: 9)) having a length identical with the mASO by Gene Tools, LLC (Philomath, Oreg.). Endo-Porter (Gene Tools) was used to help cells incorporate the morpholino oligonucleotides.
    (Patient and Cell Line)
Leukocytes were separated from the blood of a Japanese patient who since the infantile period had clinical symptoms and biological aberrant phenotype of GSD-Ia. A homozygote of c.648G>T was searched by bidirectional sequencing of genomic DNA.

After transformation with Epstein-Barr virus (EBV), lymphoblastoid cells were maintained in RMPI 1640 culture medium containing 10% fetal calf serum (HyClone, Logan, Utah, USA), 100 U/mL penicillin, and 100 mg/mL streptomycin at 37° C. and 5% $CO_2$. Other cells derived from a healthy adult were prepared as a normal control.
    (Exposure to Antisense Oligonucleotide)
$10^5$ cells were resuspended in 200 µL of a new culture medium containing 1.0 µmol/L of either mASO or mCO and 0.8 µL of Endo-Porter. After incubation at 37° C. for 48 hours, the cells were cleaned with phosphate-buffered saline and collected.
    (RNA Preparation, RT-PCR, and Nested PCR)
Total RNA was extracted using the RNeasy kit (Qiagen, Valencia, Calif.), and cDNA was synthesized by reverse transcription reaction using a first-strand synthesis system for RT-PCR (SuperScript; Invitrogen, Carlsbad, Calif.).

Then, nested PCR was carried out to check an effect of mASO on splicing of mRNA. Primers used in nested PCR are indicated in Table 1. In first PCR, a primer set G6PC-F1/G6PC-R was used to amplify a segment containing c.648G>T. In second PCR, another primer set G6PC-F2/G6PC-R was used. An expected size of a PCR product derived from normal splicing was 305 bp, and an expected size of a PCR product derived from aberrant splicing was 214 bp. After separation by agarose gel electrophoresis, the PCR products were extracted from the agarose gel and sequenced directly using the BigDye Terminator v3.1 cycle sequencing kit (Applied Biosystems, Foster City, Calif., USA) and ABI PRISM 310 genetic analyzer (Applied Biosystems).

TABLE 1

Primers for nested PCR for the exon 4-5 boundary region of G6PC cDNA

| | |
|---|---|
| Forward primer for the first PCR (G6PC-F1; complementary to c.373G - c.393C) | 5'-GGTGTATACTACGTGATGGTC-3' (SEQ ID NO: 10) |
| Forward primer for the second PCR (G6PC-F2; complementary to c.468T - c.487A)* | 5'-TTGGGATTCTGGGCTGTGCA-3' (SEQ ID NO: 11) |
| Reverse primer for the first and the second PCR (G6PC-R; complementary to c.754C - c.773T)* | 5'-AAGGGTGTGGTGTCAATGTG-3' (SEQ ID NO: 12) |

*We referred to a previous report [Reference Literature 5] for primers G6PC-F2 and G6PC-R.

Figure 2:
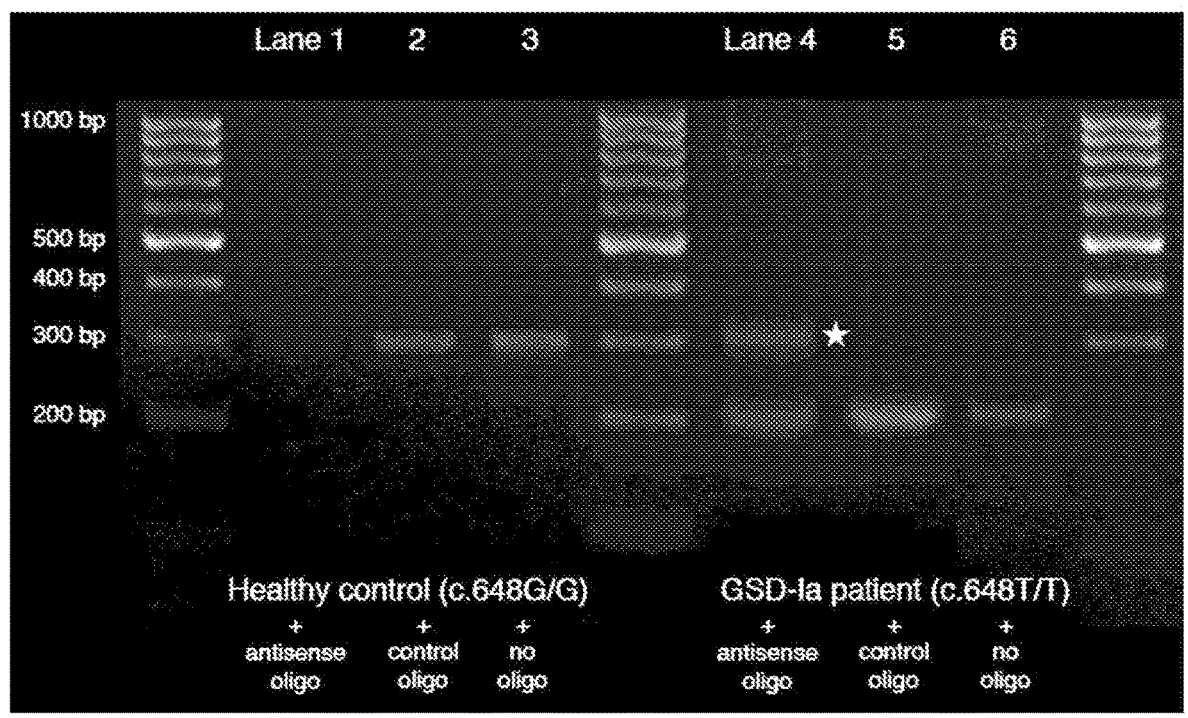
FIG. 2 is a view showing results of agarose gel electrophoresis of nested PCR products derived from a healthy control subject (lanes 1 through 3) and from a GSD-Ia patient (lanes 4 through 6).

=Result=
    (Agarose Gel Electrophoresis of Nested PCR Product)
FIG. 2 is a view showing results of agarose gel electrophoresis on nested PCR products derived from a healthy control subject (lanes 1 through 3) and from a GSD-Ia patient (lanes 4 through 6).

In lanes 1 through 3, single bands having respective lengths of approximately 300 bp were seen. In lanes 5 and 6, single bands having respective lengths of approximately 200 bp were seen. In lane 4, both the bands were observed. At the star mark in lane 4, a longer band of nested PCR product was seen. This indicates restoration of aberrant splicing of G6PC c.648G>T by the morpholino antisense oligonucleotide.

Figure 3:
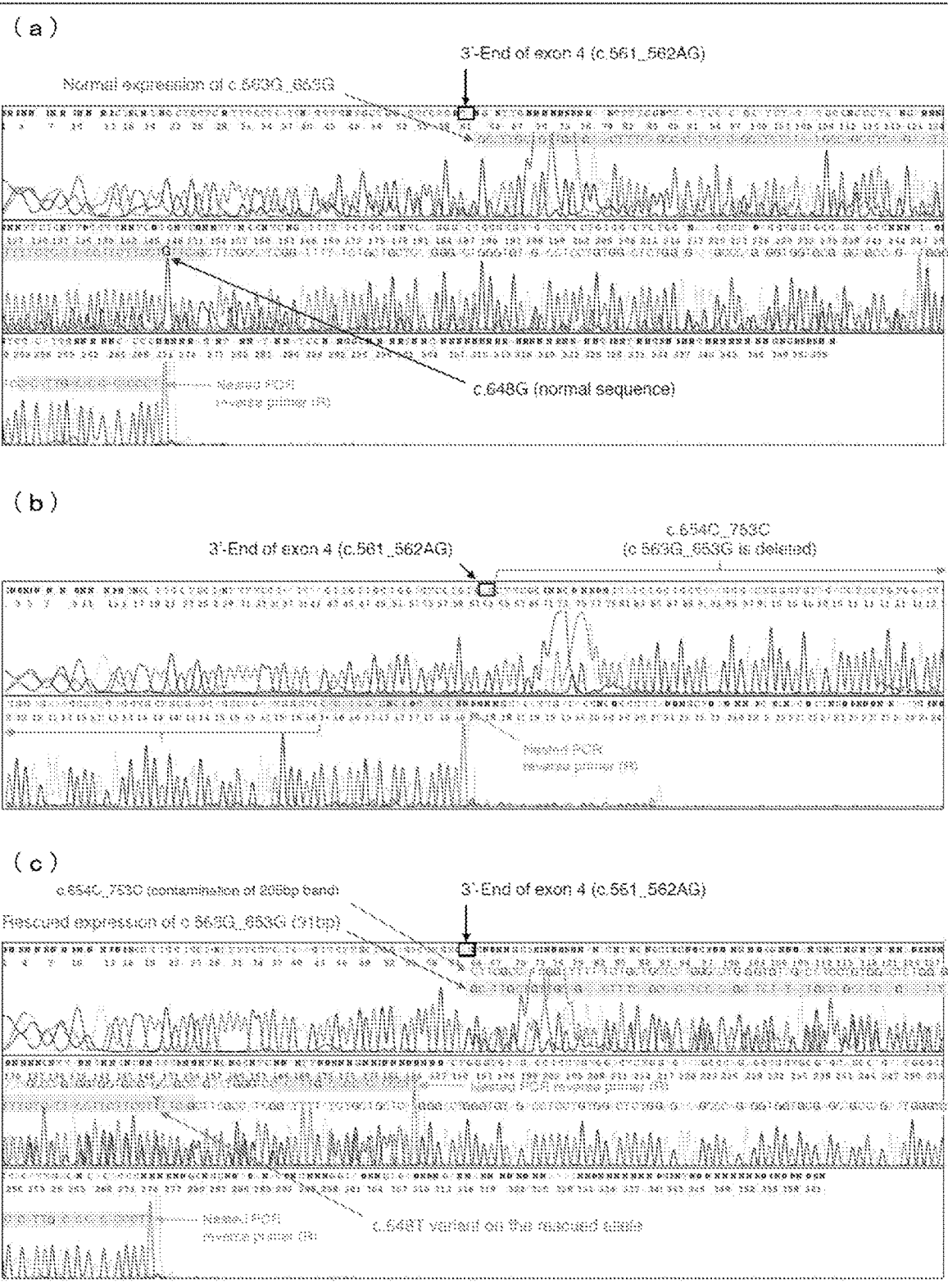
FIG. 3 is a view showing results of direct sequencing of nested PCR products. (a) of FIG. 3 shows a sequence of a single band (305 bp) in lanes 1 through 3. (b) of FIG. 3 shows a sequence of a single band (214 bp) in lanes 5 and 6 and a sequence of a shorter band (214 bp) in lane 4. (c) of FIG. 3 shows a sequence of a longer band (305 bp) in lane 4.

Then, the nested PCR products shown in FIG. 2 were extracted from the gel and sequenced directly. FIG. 3 is a view showing results of direct sequencing of nested PCR products. (a) of FIG. 3 shows a sequence of a single band (305 bp) in lanes 1 through 3. A normal exon 5 (c.563G_753C) continues from the 3' end (c.561_562AG) of exon 4. (b) of FIG. 3 shows a sequence (214 bp) of a single band in lanes 5 and 6 and a sequence of a shorter band (214 bp) in lane 4. c.654C_753C continue from the 3' end (c.561_562AG) of exon 4. This indicates deletion of 91 bp (c.563G_653C). (c) of FIG. 3 shows a sequence of a longer band (305 bp) in lane 4. Though there was contamination by the fragments of the shorter band, the 3' end of exon 4 (c.561_562AG) was followed by c.563G_753C, where c.648T was substituted for c.648G.

In the normal control sample, no difference was found among the samples treated with mASO or mCO, or depending on whether or not the samples were treated. In all the samples, single bands of approximately 300 bp appeared. Similarly, each of the patient samples treated with mCO or without treatment produced a single band of approximately 200 bp. Comparatively, the patient sample treated with mASO generated two bands of approximately 200 bp and approximately 300 bp. This suggests partial restoration of normal splicing in the patient sample (see FIG. 3).

In the normal control sample, the sequence of the binding region of exon 4 and exon 5 was normal with either mASO or mCO treatment. On the contrary, in the patient sample, 91 bp deletion was observed in the samples which had the respective bands of approximately 200 bp and were treated with mCO or not treated. The band of approximately 300 bp of the sample treated with mASO contained two kinds of DNA fragments. One of the two kinds of DNA fragments showed a sequence as cDNA having a normal length and containing base substitution c.648T, and the other of the two kinds of DNA fragments showed a sequence having an aberrant length including the 91 bp deletion. This may have been because the fragment which had an aberrant length and was located downstream from the cDNA fragment having a normal length has caused contamination during the agarose gel electrophoresis process.

=Discussion=

Antisense oligonucleotides have been widely shown to restore splicing variations for various inherited diseases, including inborn errors of metabolism (see Reference Literature 1). Among various types of ASO molecules, morpholino ASO can be administered and delivered effectively in vivo. Among various types of ASO molecules, morpholino ASO can be administered and delivered effectively in vivo by conjugation with a dendritic molecule transporter. Intravenous administration of the complex of the dendritic molecule transporter and the morpholino ASO to transgenic mice harboring a splicing variation in the intron of the globin gene has been shown to restore normal mRNA almost completely in the skeletal muscle, liver, kidneys and small intestine. On the contrary, the effect has been hardly seen in the spleen, heart, lungs and brain (see Reference Literature 3). G6PC expresses G6Pase only in the liver, kidneys and small intestine, and it is therefore expected that GSD-Ia caused by the G6PC c.648G>T variant can be a good target for ASO-based therapy.

Generally, it can be difficult to put this type of chemical agent into practical use, because many of these variants in the inherited diseases are sporadic and therefore cannot be good targets for pharmaceutical development. However, the G6PC c.648G>T variant is a good target for ASO therapy.

The aberrant splicing caused by this variant was reported for the first time in liver tissues of affected patients (see Reference Literature 4), followed by another report of successful observation in EBV-transformed lymphoblastoid cells (see Reference Literature 5). After these findings were made, it has been shown that the frequency of this variant allele is quite high among East Asian populations (see Table 2). In Japan, 80% to 85% of affected populations were homozygotes of G6PC c.648G>T, and the remainder were mainly heterozygotes of c.648G>T and sporadic variants (see Reference Literatures 5 and 6).

TABLE 2

Previous reports on the frequency of G6PC c.648G > T variant among East Asian populations

| | | Number of GSD-Ia patients | | | Rate of patients with at least one allele of c.648G > T (%) |
|---|---|---|---|---|---|
| Author | Nationality | Total | c.648G > T Homo | c.648G > T Hetero | |
| Akanuma* [Reference 5] | Japanese | 51 | 40 | 8 | 94.1 |
| Kido* [Reference 6] | Japanese | 36 | 29 | 6 | 97.2 |
| Ki [Reference 9] | Korean | 13 | 9 | 3 | 92.3 |
| Chiang (Taiwan) [Reference 7] | Chinese | 44 | 18 | 21 | 88.6 |
| Qiu (mainland China) [Reference 8] | | | | | |

*These two studies seem to have a partial overlap of patients.

From these, it is supposed that approximately 95% of Japanese GSD-Ia patients have this variant in at least one allele. According to several reports on the detection of this variant from Taiwan (see Reference Literature 7), mainland China (see Reference Literature 8) and South Korea (see Reference Literature 9), the rates of patients with at least one allele of c.648G>T were 92.3% among Koreans and 88.6% among Chinese.

These findings suggest that a great majority of GSD-Ia patients in the countries listed above will benefit from a single ASO-based therapeutic agent. Whether or not ASO can improve the pathologic changes observed in affected patients would be confirmed, for example, by establishing induced pluripotent stem (iPS) cell lines that are derived from GSD-Ia patients having c.648G>T variant G6PC and differentiating those cells into hepatocyte-like cells presenting intracellular accumulation of glycogen (see Reference Literature 10).

As above described, the present invention is accomplished based on the quite effective finding for establishing a novel medicine specific for GSD-Ia.

List of Reference Literatures in Example 1

[Reference Literature 1] M. A. Havens, D. M. Duelli, M. L. Hastings, Targeting RNA splicing for disease therapy, Wiley Interdiscip. Rev. RNA 4 (3) (2013) 247-266.
[Reference Literature 2] J. Y. Chou, B. C. Mansfield, Mutations in the Glucose-6-Phosphatase-α (G6PC) gene that cause type Ia glycogen storage disease, Hum. Mutat. 29 (7) (2008) 921-930.
[Reference Literature 3] Y. F. Li, P. A. Morcos, Design and synthesis of dendritic molecular transporter that achieves efficient in vivo delivery of morpholino antisense oligo, Bioconjugate Chem. 19 (7) (2008) 1464-1470.
[Reference Literature 4] S. Kajihara, S. Matsuhashi, K. Yamamoto, K. Kido, K. Tsuji, A. Tanae, S. Fujiyama, T. Itoh, K. Tanigawa, M. Uchida, Y. Setoguchi, M. Motomura, T. Mizuta, T. Sakai, Exon redefinition by a point mutation within exon 5 of the glucose-6-phosphatase gene is the major cause of glycogen storage disease type Ia in Japan, Am. J. Hum. Genet. 57 (3) (1995) 549-555.
[Reference Literature 5] J. Akanuma, T. Nishigaki, K. Fujii, Y. Matsubara, K. Inui, K. Takahashi, S. Kure, Y. Suzuki, T. Ohura, S. Miyabayashi, E. Ogawa, K. Iinuma, S. Okada, K. Narisawa, Glycogen storage disease type 1a: molecular diagnosis of 51 Japanese patients and characterization of splicing mutations by analysis of ectopically transcribed mRNA from lymphoblastoid cells, Am. J. Med. Genet. 91 (2) (2000) 107-112.
[Reference Literature 6] J. Kido, K. Nakamura, S. Matsumoto, H. Mitsubuchi, T. Ohura, Y. Shigematsu, T. Yorifuji, M. Kasahara, R. Horikawa, F. Endo, Current status of hepatic glycogen storage disease in Japan: clinical manifestations, treatments and long-term outcomes. J. Hum. Genet. 58 (5) (2013) 285-292.
[Reference Literature 7] S. C. Chiang, Y. M. Lee, M. H. Chang, T. R. Wang, T. M. Ko, W. L. Hwu, Glucose-6-phosphatase gene mutations in Taiwan Chinese patients with glycogen storage disease type 1a, J. Hum. Genet. 45 (4) (2000) 197-199.
[Reference Literature 8] W. J. Qiu, X. F. Gu, J. Ye, L. S. Han, Y. F. Zhang, X. Q. Liu, Molecular genetic analysis of glycogen storage disease type Ia in 26 Chinese patients, J. Inherit. Metab. Dis. 26 (8) (2003) 811-812.
[Reference Literature 9] C. S. Ki, S. H. Han, H. J. Kim, S. G. Lee, E. J. Kim, J. W. Kim, Y. H. Choe, J. K. Seo, Y. J. Chang, J. Y. Park, Mutation spectrum of the glucose-6-phosphatase gene and its implication in molecular diagnosis of Korean patients with glycogen storage disease type Ia, Clin. Genet. 65 (6) (2004) 487-489.
[Reference Literature 10] S. T. Rashid, S. Corbineau, N. Hannan, S. J. Marciniak, E. Miranda, G. Alexander, I. Huang-Doran, J. Griffin, L. Ahrlund-Richter, J. Skepper, R. Semple, A. Weber, D. A. Lomas, L. Vallier, Modeling inherited metabolic disorders of the liver using human induced pluripotent stem cells, J. Clin. Invest. 120 (9) (2010) 3127-3136.

Example 2

With use of an LNA antisense oligonucleotide, that is, with use of an antisense oligonucleotide containing a locked nucleic acid (LNA) that is expected to bring about an effect in administration to the living body, an attempt was made to inhibit aberrant splicing.

=Materials and Method=

(LNA Antisense Oligonucleotide)

Under conditions below, a 15-mer LNA antisense oligonucleotide (LNA ASO) was designed which targeted an ectopic splice acceptor site of aberrant splicing in pre-mRNA of c.648G>T variant G6PC. Seven types of LNA ASO were designed each of which had a complementary sequence to the 15-mer sequence included in the region from c.639C to c.665G in the G6PC sequence in which c.648G was substituted by c.648T. The seven types of LNA ASO were LNA01, LNA03, LNA05, LNA07, LNA09, LNA11, and LNA13. The synthesis was carried out by contract synthesis (GeneDesign, Inc., Ibaraki-shi, Osaka).

(Design Conditions of LNA ASO)

The base length was 15 bases, and LNA was introduced at alternative residues (as indicated by shaded parts in Table 3).

The bases at the 3' end and 5' end were native DNA.

The bases were bound by phosphorothioate (PS) linkage.

The designed regions were staggered by 2 bases.

TABLE 3

| 15-mer LNA antisense oligonucleotide used in Example 2 | | |
|---|---|---|
| | 5'-TCCGATGGCGAAGCTGAAAAGGAAGAAG-3' | (SEQ ID NO: 16) |
| LNA01 | 5'-CTGAAAAGGAAGAAG-3' | (SEQ ID NO: 17) |
| LNA03 | 5'-AGCTGAAAAGGAAGA-3' | (SEQ ID NO: 18) |
| LNA05 | 5'-GAAGCTGAAAAGGAA-3' | (SEQ ID NO. 19) |
| LNA07 | 5'-GCGAAGCTGAAAAGG-3' | (SEQ ID NO: 20) |
| LNA09 | 5'-TGGCGAAGCTGAAAA-3' | (SEQ ID NO: 21) |
| LNA11 | 5'-GATGGCGAAGCTGAA-3' | (SEQ ID NO: 22) |
| LNA13 | 5'-CCGATGGCGAAGCTG-3' | (SEQ ID NO: 23) |

(Cell Line)

From a patient affected by glycogen storage disease type Ia (homozygote) who had been identified to have c.648G>T variant, peripheral blood lymphocytes were taken and infected with EBV to establish immortalized lymphocyte cell lines, and the cell lines thus established were maintained by a method similar to that of Example 1.

(Transfection)

In 200 μL of a new culture medium which contained $CaCl_2$ at a final concentration of 9 mM and each of LNA01 through LNA13 at a final concentration of 1 μM, $4.5 \times 10^4$ cells were resuspended, and were then seeded onto a microplate (96 wells) having a surface coated with poly-D-lysine (Thermo Fisher Scientific, Waltham, Mass., USA). A well to which no LNA was added is indicated as blank. After the cultivation at 37° C. for 7 days to confluency, the cells were cleaned with phosphate-buffered saline and collected.

(RNA Preparation, RT-PCR, and Nested PCR)

Total RNA was extracted from the collected cells, and cDNA was synthesized. Then, nested PCR was carried out to check an effect of LNA ASO on splicing of mRNA by amplifying a sequence of a region including a c.648G>T variation site and an ectopic splice acceptor site (c.652_653AG) from a binding region between exon 4 and exon 5 of G6PC. The nested PCR was carried out with use of a primer set identical with that used in Example 1.

As with Example 1, an expected size of a PCR product derived from normal splicing was 305 bp (normal length), and an expected size of a PCR product derived from aberrant splicing was 214 bp (length after deletion). After separation by agarose gel electrophoresis, a lump containing a band having a length after deletion and a band having a normal length on the gel was taken out from the agarose gel, then DNA was extracted from the lump, and DNA was sequenced directly.

Note that, the extraction of RNA, the method for synthesizing cDNA, the agarose gel electrophoresis, and the direct sequencing in Example 2 were similar to those used in Example 1.

=Result=

(Agarose Gel Electrophoresis of Nested PCR Product)

Figure 4:
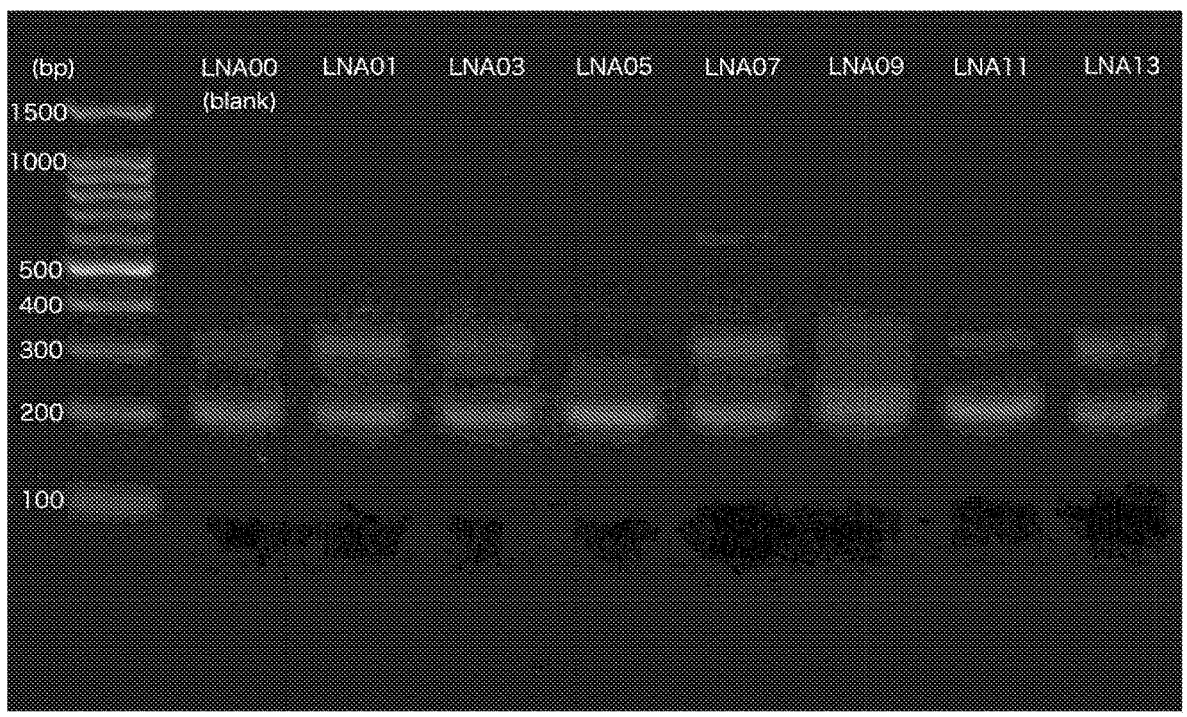
FIG. 4 shows results of agarose gel electrophoresis on nested PCR products of samples in which LNA ASOs (LNA01 through LNA13) have been added and no LNA ASO has been added (blank).

FIG. 4 shows results of agarose gel electrophoresis on nested PCR products of samples in which LNA ASOs have been added (LNA01 through LNA13) and no LNA ASO has been added (blank).

In each of the LNA ASO added samples, both bands were observed. This indicates restoration by LNA ASO from aberrant splicing of G6PC c.648G>T, and it was expected that, as the normal length band intensity was higher, the effect of restoration by LNA ASO from aberrant splicing was higher.

Figure 5:
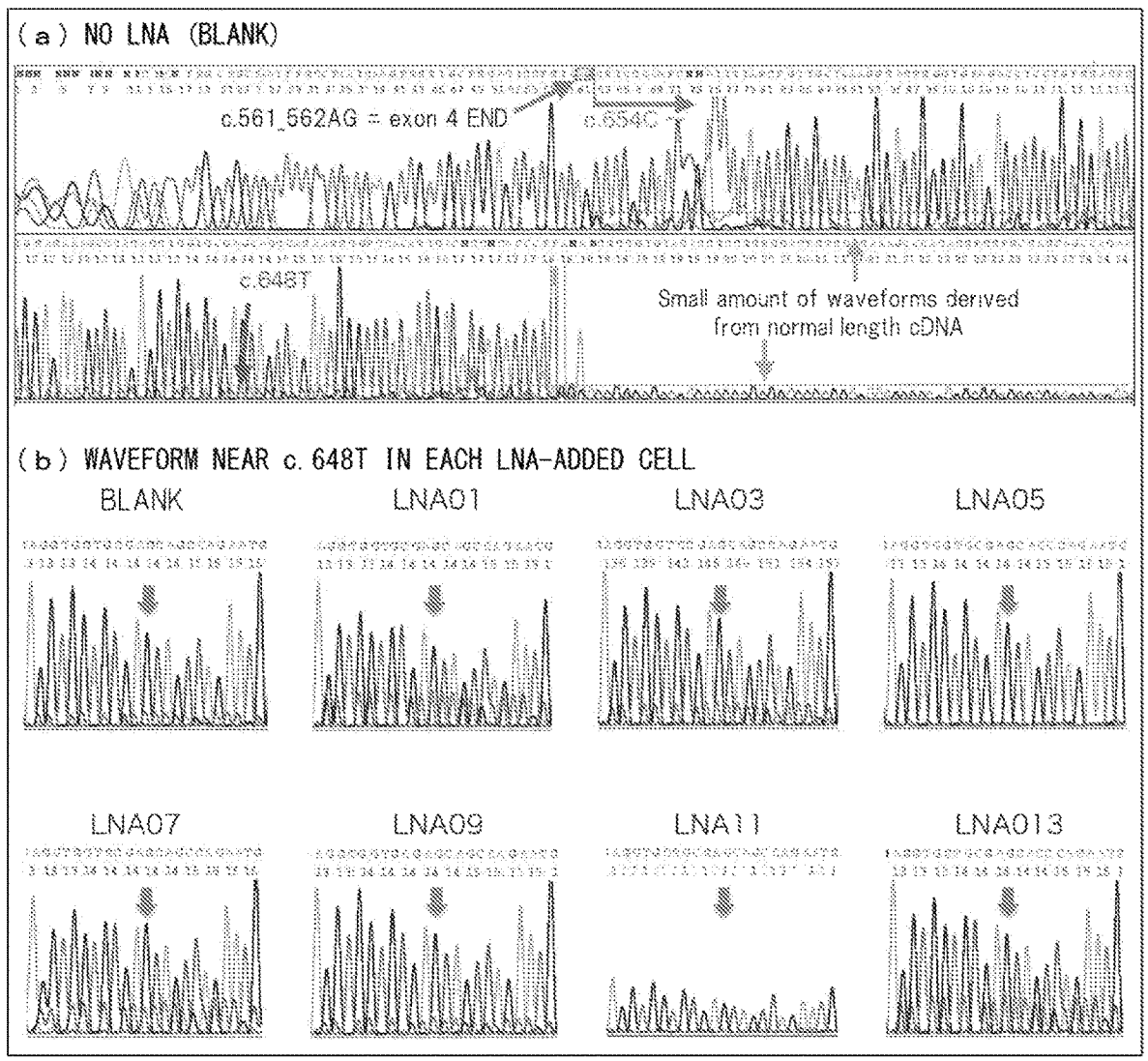
FIG. 5 is a view showing results of direct sequencing of nested PCR products. (a) of FIG. 5 shows a sequence of the nested PCR product derived from the sample in which no LNA ASO has been added. (b) of FIG. 5 shows waveforms near c.648G>T of nested PCR products derived from samples in which the respective LNA ASOs have been added.

FIG. 5 is a view showing results of direct sequencing of nested PCR products. (a) of FIG. 5 shows a sequence of the nested PCR product derived from the (LNA00) sample in which no LNA ASO has been added. (b) of FIG. 5 shows waveforms near c.648G>T of nested PCR products derived from samples in which the respective LNA ASOs have been added.

=Analysis=

It is reported that LNA ASO acts more strongly as compared with oligonucleotides having other kinds of structures, and brings about an antisense effect also in natural uptake ("gymnosis" or "free-uptake") to cells that is carried out without induction chemical agent or physical stimulation (see Reference Literatures 12 and 13). In Example 2, the analysis was carried out with this method.

In expression of c.648G>T variant G6PC by aberrant splicing in the EBV immortalized lymphocyte cell line, a small amount of normal expression product by normal splicing was also generated voluntarily.

It is suggested that there is a correlation between (i) intensity of the band having a normal length with respect to intensity of the band having a length after deletion obtained in the agarose gel electrophoresis and (ii) a relative relationship between a wave height derived from deletion band and a wave height derived from normal length band in extraction from gel. From these, among LNA01 through LNA13, LNA01, LNA07, and LNA13 are particularly promising as candidates of LNA ASO.

List of Reference Literatures in Example 2

[Reference Literature 11] Shimo T, Tachibana K, Saito K, Yoshida T, Tomita E, Waki R, Yamamoto T, Doi T, Inoue T, Kawakami J, Obika S, Design and evaluation of locked nucleic acid-based splice-switching oligonucleotides in vitro, Nucleic Acids Res. 42 (12) (2014) 8174-8187.

[Reference Literature 12] Soifer H S, Koch T, Lai J, Hansen B, Hoeg A, Oerum H, Stein C A, Silencing of gene expression by gymnotic delivery of antisense oligonucleotides, Methods Mol. Biol. 815 (2012) 333-346.

[Reference Literature 13] Hori S, Yamamoto T, Waki R, Wada S, Wada F, Noda M, Obika S, Ca2+ enrichment in culture medium potentiates effect of oligonucleotides, Nucleic Acids Res. 43 (19) (2015) e128.

INDUSTRIAL APPLICABILITY

The present invention is applicable to, for example, prevention or treatment of glycogen storage disease type Ia.

The invention claimed is:

1. A method for treating glycogen storage disease type Ia in a subject, comprising administering to the subject a therapeutically effective amount of an antisense oligonucleotide,
  wherein the antisense oligonucleotide is capable of hybridizing with a pre-mRNA sequence of c.648G>T variant G6PC gene at a region (hybridizing region) including at least one of the following base in a base sequences of human chromosome 17 of GRCh38/hg38:
  a base at position 42911000 (which corresponds to position 648 in cDNA sequence of c.648G>T variant G6PC, the cDNA sequence being a base sequence shown in SEQ ID NO: 4 in which guanine (G) at position 648 is substituted by thymine (T)),
  a base at position 42911004 (which corresponds to position 652 in cDNA sequence of c.648G>T variant G6PC, the cDNA sequence being a base sequence shown in SEQ ID NO: 4 in which guanine (G) at position 648 is substituted by thymine (T)), and
  a base at position 42911005 (which corresponds to position 653 in cDNA sequence of c.648G>T variant G6PC, the cDNA sequence being a base sequence shown in SEQ ID NO: 4 in which guanine (G) at position 648 is substituted by thymine (T)),
  wherein the antisense oligonucleotide is capable of inhibiting aberrant splicing of pre-mRNA of c.648G>T variant G6PC,
  wherein the antisense oligonucleotide is a single-strand nucleotide made up of 7 to 104 bases consisting of a base sequence completely complementary to the hybridizing region in the pre-mRNA of c.648G>T variant G6PC gene.

2. The method of claim 1, wherein said hybridizing region is within a region of the pre-mRNA of c.648G>T variant G6PC gene corresponding to bases at positions 42910951 to 42911054 (which corresponds to positions 599 to 702 in cDNA sequence of c.648G>T variant G6PC, the cDNA sequence being a base sequence shown in SEQ ID NO: 4 in which guanine (G) at position 648 is substituted by thymine (T)) in a base sequence of human chromosome 17 of GRCh38/hg38.

3. The method of claim 1 wherein said antisense oligonucleotide is made up of 15 to 64 bases.

4. The method of claim 1, wherein said antisense oligonucleotide is (a) below:
  (a) an antisense oligonucleotide including a base sequence shown in SEQ ID NO: 14, SEQ ID NO: 17, SEQ ID NO: 20, or SEQ ID NO: 23.

5. The method of claim 1, wherein said antisense oligonucleotide
  is a morpholino antisense oligonucleotide being made up of 14 to 30 bases and containing at least one morpholino nucleotide, or
  is a locked nucleic acid (LNA) antisense oligonucleotide being made up of 7 to 25 bases and containing at least one locked nucleic acid.

6. The method of claim 1, wherein said hybridizing region is within a region of the pre-mRNA of c.648G>T variant G6PC gene corresponding to bases at positions 42910971 to 42911034 (which corresponds to positions 619 to 682 in cDNA sequence of c.648G>T variant G6PC, the cDNA sequence being a base sequence shown in SEQ ID NO: 4 in which guanine (G) at position 648 is substituted by thymine (T)) in a base sequence of human chromosome 17 of GRCh38/hg38.

7. The method of claim 1, wherein said antisense oligonucleotide is made up of 15 to 30 bases.

8. The method of claim 1, wherein said antisense oligonucleotide contains at least one modified nucleotide.

* * * * *